(12) United States Patent
Wang et al.

(10) Patent No.: US 9,724,385 B2
(45) Date of Patent: *Aug. 8, 2017

(54) STIP1 POLYPEPTIDES AND USES THEREOF

(71) Applicant: Chang Gung Memorial Hospital, Linkou Branch, Gueishan Township (TW)

(72) Inventors: Tzu-Hao Wang, Gueishan Township (TW); Chia-Lung Tsai, Gueishan Township (TW); Angel Chao, Gueishan Township (TW)

(73) Assignee: Chang Gung Memorial Hospital, Linkou Branch, Gueishan Township (TW)

( * ) Notice: Subject to any disclaimer, the term of this patent is extended or adjusted under 35 U.S.C. 154(b) by 0 days.

This patent is subject to a terminal disclaimer.

(21) Appl. No.: 14/813,249

(22) Filed: Jul. 30, 2015

(65) Prior Publication Data
US 2016/0008426 A1    Jan. 14, 2016

Related U.S. Application Data

(63) Continuation of application No. 14/172,017, filed on Feb. 4, 2014, now Pat. No. 9,145,449.

(60) Provisional application No. 61/760,597, filed on Feb. 4, 2013.

(51) Int. Cl.
| | | |
|---|---|---|
| *A61K 38/00* | (2006.01) | |
| *A61K 38/17* | (2006.01) | |
| *C07K 14/47* | (2006.01) | |
| *C07K 16/18* | (2006.01) | |
| *A61K 39/395* | (2006.01) | |
| *A61K 39/00* | (2006.01) | |

(52) U.S. Cl.
CPC ...... *A61K 38/1709* (2013.01); *A61K 39/3955* (2013.01); *C07K 14/47* (2013.01); *C07K 16/18* (2013.01); *A61K 2039/505* (2013.01); *C07K 2317/34* (2013.01); *C07K 2317/76* (2013.01)

(58) Field of Classification Search
None
See application file for complete search history.

(56) References Cited

U.S. PATENT DOCUMENTS 6,812,339 B1 * 11/2004 Venter .......... C12Q 1/6883
                                          435/6.11
9,145,449 B2 * 9/2015 Wang ............ A61K 39/3955

FOREIGN PATENT DOCUMENTS

WO    2010/115118    * 10/2010

OTHER PUBLICATIONS

Strome et al., The Oncologist, 2007; 12:1084-95.*
Brand et al., Anticancer Res. 2006; 26:463-70.*
Johnson et al Cancer Treatment Reviews vol. 2 p. 1 (1975).*
Burgess et al, Journal of Cell Biology vol. 111 Nov. 1990 2129-2138.*
Lazar et al Molecular and Cellular Biology Mar. 1988 vol. 8 No. 3 1247-1252.*
Tsai et al Cell Reports vol. 2 p. 283 (Aug. 30, 2012).*
Skolnick et al. (Trends in Biotech., 18(1):34-39, 2000).*

* cited by examiner

*Primary Examiner* — Sheela J Huff
(74) *Attorney, Agent, or Firm* — Osha Liang LLP

(57) ABSTRACT

The present invention is directed toward pharmaceutical compositions comprising an isolated polypeptide and a pharmaceutically acceptable carrier. The present invention also discloses an antibody or an antigen-binding portion thereof that bind to the isolated polypeptide. Methods of inhibiting cancer cells growth are also disclosed, comprising administering the isolated polypeptide or the antibody described herein to a subject in need thereof.

6 Claims, 18 Drawing Sheets
(7 of 18 Drawing Sheet(s) Filed in Color)

Peptides of stress-induced-phosphoprotein 1 (STIP1, IPI00013894.1) identified in the conditioned media of various cancer cell lines.

| Nasopharyngeal carcinoma cell line NPC-TW04: Seq. coverage 19.3% | Lung adenocarcinoma cell line CL1-5 Seq. coverage: 25.8% | Heptocellular cacinoma cell line Hep 3B Seq. coverage: 35% |
|---|---|---|
| Identified peptides: | Identified peptides: | Identified peptides: |
| DPQALSEHLK | AAALEFLNR | HYTEAIK |
| AMADPEVQQIMSDPAMR | EGLQNMEAR | AAALEFLNR |
| AAALEFLNR | DCEECIQLEPTFIK | EGLQNMEAR |
| TYEEGLKHEANNPQLK | TYEEGLKHEANNPQLK | DCEECIQLEPTFIK |
| LILEQMQK | LMDVGLIAIR | TYEEGLKHEANNPQLK |
| LDPHNHVLYSNR | LLEFQLALK | NPVIAQK |
| LAYINPDLALEEK | KAAALEFLNR | TLLSDPTYR |
| LMDVGLIAIR | ALDLDSSCK | LMDVGLIAIR |
| NPVIAQKIQKLMDVGLIAIR | DPQALSEHLK | HDGPEDVKR |
| | LILEQMQK | DPQALSEHLK |
| | FMNPFNMPNLYQK | AMADPEVQQIMSDPAMR |
| | ALSVGNIDDALQCYSEAIK | DAIHFYNK |
| | LAYINPDLALEEK | KDFDTALK |
| | | FMNPFNMPNLYQK |
| | | ALSVGNIDDALQCYSEAIK |
| | | LDPHNHVLYSNR |
| | | LAYINPDLALEEK |

Figure 2

Fig. 7A
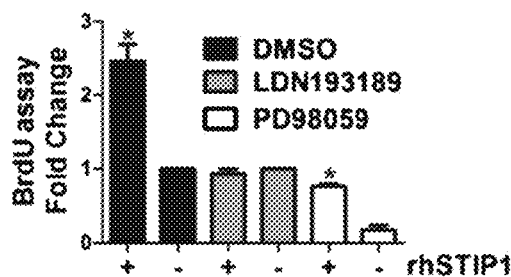
Fig. 7B Ki67 immunocytochemistry
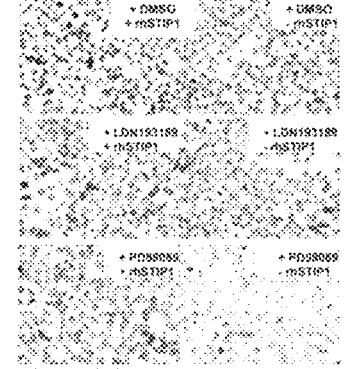
Fig. 7C
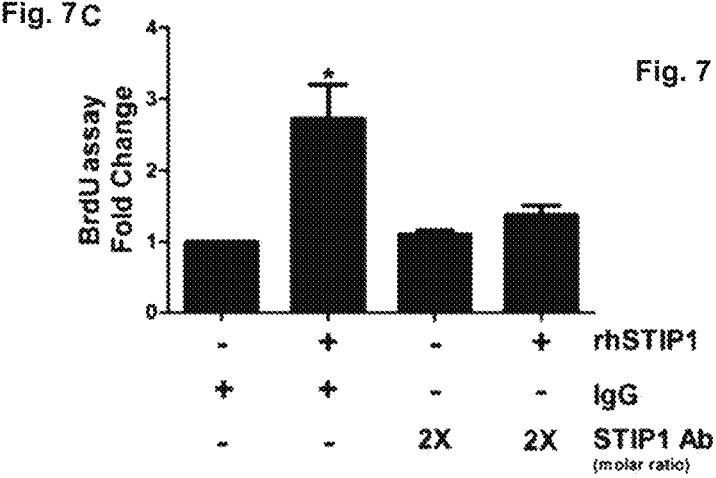
Fig. 7D Ki67 immunocytochemistry
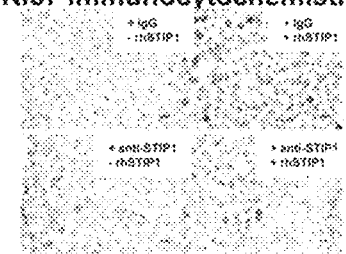
Fig. 7E
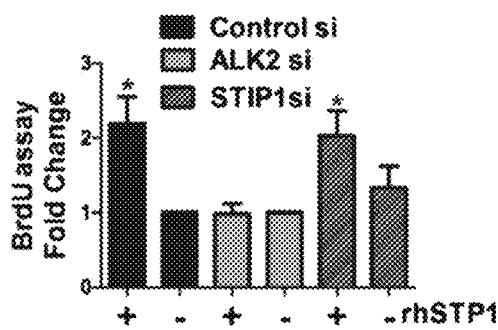
Fig. 7F Ki67 immunocytochemistry
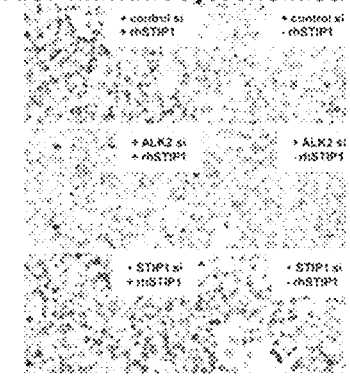

Fig. 11A
Fig. 11B
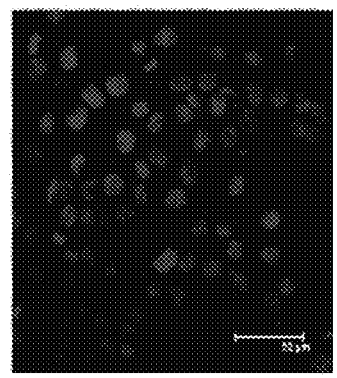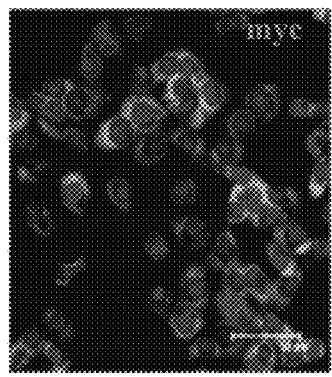

Fig. 15A.
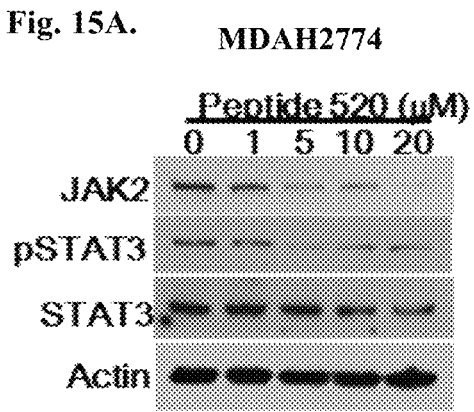
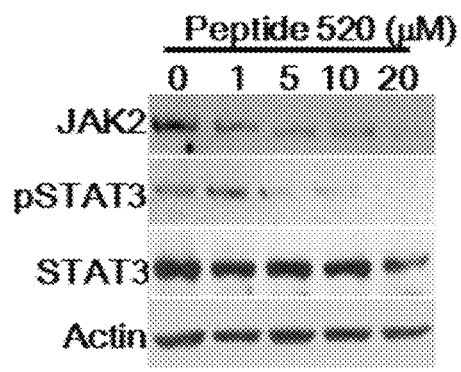
Fig. 15B.
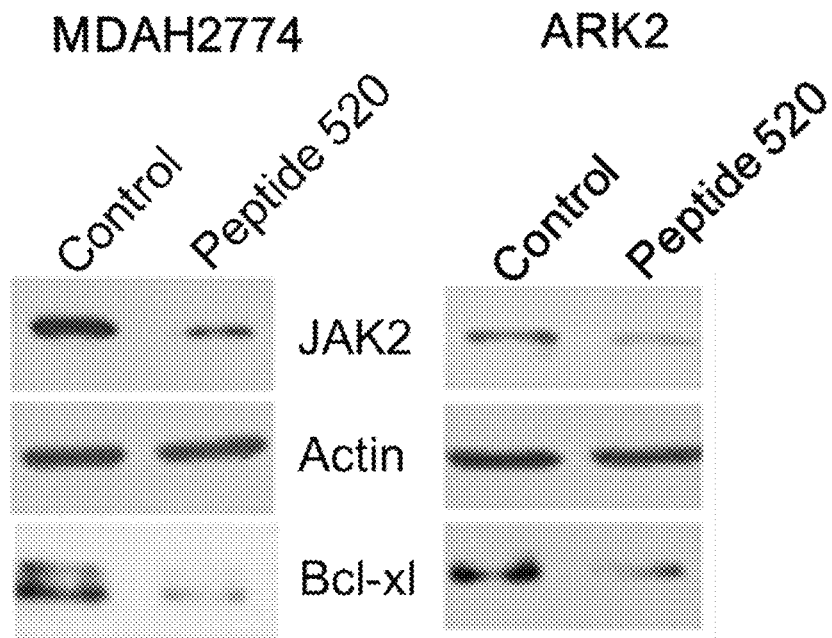

STIP1 POLYPEPTIDES AND USES THEREOF

CROSS-REFERENCE TO RELATED APPLICATIONS

This application is a continuation application of U.S. application Ser. No. 14/172,017, filed on 4 Feb. 2014, which claims the benefit of U.S. Application No. 61/760,597, filed on 4 Feb. 2013, the entire disclosures of which are incorporated herein by reference.

BACKGROUND OF THE INVENTION

Stress-induced phosphoprotein (STIP1, SEQ ID NO:3) is a 62.6 kDa protein, also known as heat shock protein (HSP)-organizing protein (HOP), because it has been shown to modulate the chaperone activities of HSP 90 and HSP 70. STIP1 contains nine tetratricopeptide repeat (TPR) motifs and one nuclear localization signal (NLS) (Longshaw et al., 2004). The TPR domains of STIP1 are involved in holding HSP70 and HSP90 together in the HSP90 chaperone machinery (Odunuga et al., 2004). This formation of protein complexes participates in several cellular processes, including transcription, protein folding, protein translocation, viral replication, signal transduction, and cell division.

Cancer remains a major public health problem worldwide. It profoundly affects more than 1 million people in the U.S. diagnosed each year, as well as their families and friends. Despite the advance in chemotherapy over the last 50 years, the medical community is still faced with the challenge for curing many different types of cancer. Accordingly, there is still a need for the development of effective and safe treatments for various types of cancer. The present invention addresses this need.

BRIEF SUMMARY OF THE INVENTION

In one embodiment, the present invention discloses a pharmaceutical compositions comprising an isolated polypeptide, where the isolated polypeptide comprises an amino acid sequence at least 90% homologous to SEQ ID NO:1. The pharmaceutical composition can further comprise an antibody against STIP1.

In another embodiment, the present invention discloses an antibody, or an antigen-binding portion which binds to an amino acid sequence at least 90% homologous to SEQ ID NO:1.

In yet another embodiment, the present invention provides a pharmaceutical composition comprising an antibody or an antigen-binding portion which binds to an amino acid sequence at least 90% homologous to SEQ ID NO:1; and a pharmaceutically acceptable carrier.

The present invention is also directed to methods for inhibiting cancer cell growth, comprising administering (i) an isolated polypeptide comprising an amino acid sequence at least 90% homologous to SEQ ID NO:1 to a subject in need thereof or (ii) an antibody or an antigen-binding portion thereof binding to an amino acid sequence at least 90% homologous to SEQ ID NO:1 to a subject in need thereof.

The invention also discloses an isolated polypeptide, comprising an amino acid sequence at least 90% homologous to SEQ ID NO:1.

The invention will become more apparent when read with the accompanying figures and detailed description which follow.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2 illustrates the presence of various STIP1 polypeptides (SEQ ID NOS: 4-25) in nasopharyngeal cancer (NPT-TWO4), lung cancer (CL1-5), and hepatocellular carcinoma (Hep3B).

FIG. 7A illustrates the effect of DMSO, ALK inhibitors (LDN193189) and ERK inhibitor (PD98059) on BrdU incorporation.

FIG. 7B illustrates the effect of DMSO, ALK inhibitors (LDN193189) and ERK inhibitor (PD98059) on Ki67 immunocytochemistry.

FIG. 7C illustrates the effect of rhSTIP1, control IgG as compared with STIP1 antibody on BrdU incorporation.

FIG. 7D illustrates the effect of control IgG as compared with STIP1 antibody on Ki67 immunocytochemistry.

FIG. 7E illustrates the effect of control siRNA, ALK2 siRNA and STIP1siRNA on BrdU incorporation.

FIG. 7F illustrates the effect of control siRNA, ALK2 siRNA and STIP1siRNA on Ki67 immunocytochemistry.

FIG. 11A and FIG. 11B are microscopic images illustrating the presence of STIP1 polypeptide 520-543 in the cytosol of the ovarian cancer cells.

FIG. 15 is an assembly of Western Blot images. FIG. 15 A shows the effect of various concentrations of STIP1 polypeptide 520-543 (peptide 520) on JAK2 and pSTAT3 proteins in ovarian and endometrial cancer cells. FIG. 15B shows the effect of STIP1 polypeptide 520-543 (peptide 520) on JAK2 and Bcl-x1 proteins.

DETAILED DESCRIPTION OF THE INVENTION

Definition

Figure 1:
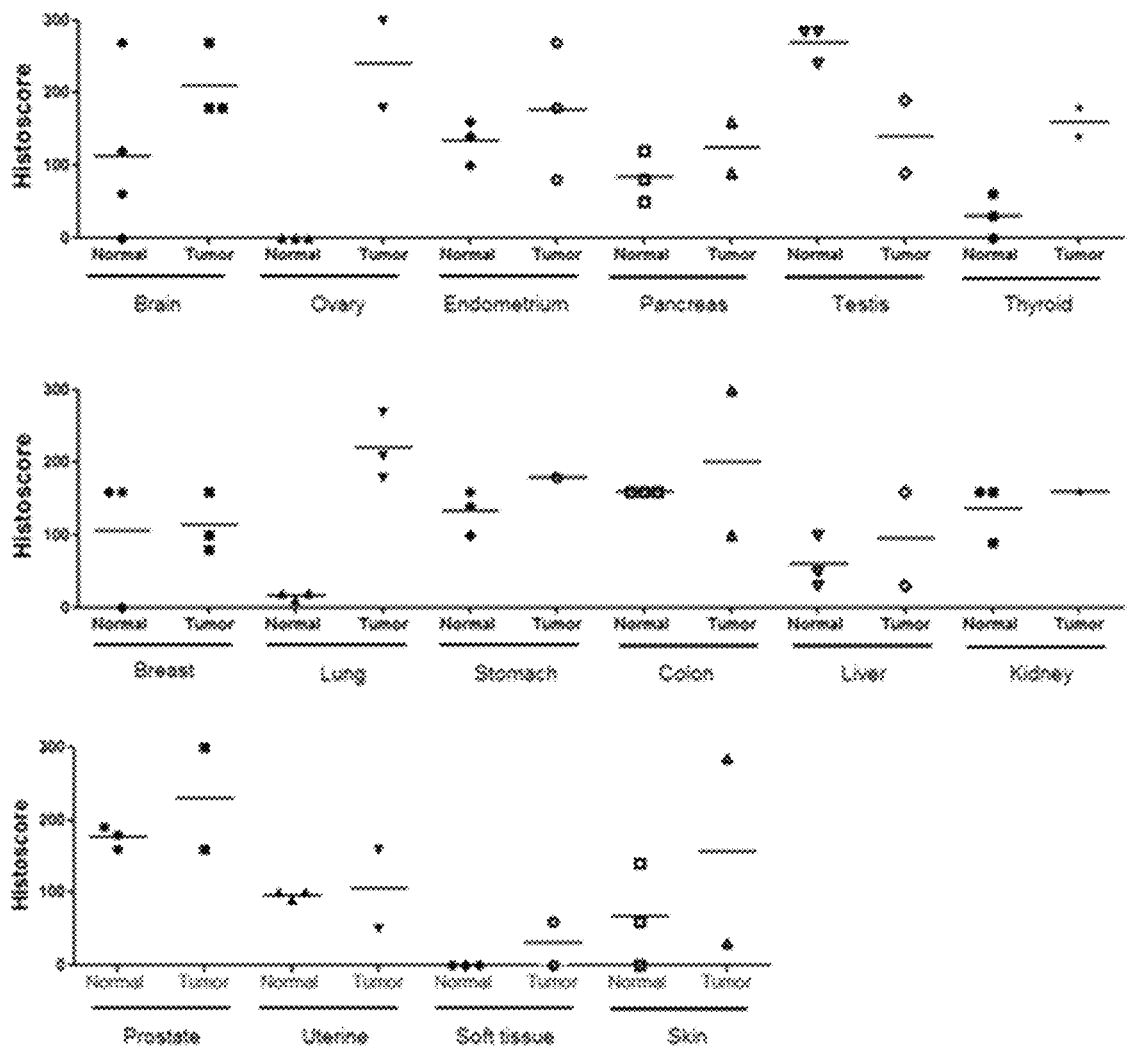
FIG. 1 illustrates the immunohistochemical analysis of STIP1 (expressed as histoscore) in various cancer cells and the corresponding normal tissues.

As employed above and throughout the disclosure, the following terms, unless otherwise indicated, shall be understood to have the following meanings As used herein, the singular forms "a," "an," and "the" include the plural reference unless the context clearly indicates otherwise.

An "effective amount," as used herein, includes a dose of an agent that is sufficient to reduce the symptoms and signs of cancer, which include, but are not limited to, weight loss, pain and tumor mass, which is detectable, either clinically as a palpable mass or radiologically through various imaging means, such as pain, weight loss or mass demonstrated on radiological images. Alternatively, an effective amount of the agent may be assessed using any other diagnostic means such as serum detection of circulating antigens or other tumor markers using an antibody-based assay (e.g., ELISA).

The term "treating," "treated," or "treatment" as used herein includes preventative (e.g. prophylactic), palliative, and curative uses or results.

The term "inhibiting" and "suppressing" includes, but is not limited to, decreasing, slowing or stopping the growth of The term "subject" as used herein includes, but is not limited to, an organism such as a mammal, e.g., a human, non-human primate (e.g., baboon, orangutan, monkey), mouse, pig, cow, goat, cat, rabbit, rat, guinea pig, hamster, horse, monkey, sheep, or other non-human mammal; a non-mammal, including, e.g., a non-mammalian vertebrate, such as a bird (e.g., a chicken or duck) or a fish, and a non-mammalian invertebrate. Preferably, the subject is a human.

All numbers herein may be understood to be modified by "about."

The terms "STIP antibody" and "antibody against STIP1" are used interchangeably.

In an embodiment, one or more of the therapeutic agents that can be used in the methods of the present invention for preventing and/or treating conditions discussed above are formulated with a pharmaceutically acceptable carrier, vehicle or adjuvant. The term "pharmaceutically acceptable carrier, vehicle or adjuvant" refers to a carrier, vehicle or adjuvant that may be administered to a patient, together with the present compounds, and which does not destroy the pharmacological activity thereof and is nontoxic when administered in doses sufficient to deliver a therapeutic amount of the compound.

The compound may be formulated as a salt such as a pharmaceutically acceptable salt form, which includes, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Pharmaceutically acceptable salts also include base addition salts which may be formed when acidic protons present are capable of reacting with inorganic or organic bases. Suitable pharmaceutically-acceptable base addition salts include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, trimethylamine. All of these salts may be prepared by conventional means from the corresponding compound of the invention by reacting, for example, the appropriate acid or base with the compound of the invention. *Handbook of Pharmaceutical Salts: Properties, and Use* (P. H. Stahl & C. G. Wermuth eds., Verlag Helvetica Chimica Acta, 2002) [1].

Pharmaceutically acceptable carriers, adjuvants and vehicles that may be used in the dosage forms of this invention include, but are not limited to, ion exchangers, alumina, aluminum stearate, lecithin, self-emulsifying drug delivery systems (SEDDS) such as d-E-tocopherol polyethyleneglycol 1000 succinate; surfactants used in pharmaceutical dosage forms such as Tweens or other similar polymeric delivery matrices; serum proteins such as human serum albumin; buffer substances such as phosphates, glycine, sorbic acid, potassium sorbate, partial glyceride mixtures of saturated vegetable fatty acids, water, salts; or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha, beta and γ-cyclodextrin, or chemically modified derivatives such as hydroxyalkylcyclodextrins, including 2- and 3-hydroxypropyl-beta cyclodextrins, or other solubilized derivatives may also be advantageously used to enhance delivery of compounds of the formulae described herein that can be used in the methods of the present invention for preventing and/or treating fibrotic conditions. Additional suitable excipients may be found in Handbook of Pharmaceutical Excipients, R. C. Rowe, et. al., Pharmaceutical Press, 2009 [9]. In certain embodiments, unit dosage formulations are compounded for immediate release, though unit dosage formulations compounded for delayed or prolonged release of one or both agents are also disclosed.

In one embodiment, the therapeutic agents that can be used in the present methods are formulated in a single unit dose such that the agents are released from the dosage at different times.

The Method of Suppressing Cancer Growth

In one embodiment, the invention is directed to methods of reducing or inhibiting cancer cell growth in a subject, the method comprising administering an isolated polypeptide which is at least 90% homologous to SEQ ID NO:1, to inhibit cancer cell growth and reduce the signs and symptoms of cancer in the subject. In one embodiment, the isolated polypeptide comprising an amino acid sequence having 90, 91, 92, 93, 94, 95, 96, 97, 98, 99 or 100% identity to the amino acid sequence shown in SEQ ID NO:1.

The isolated polypeptides can be used alone, or in combination with a STIP1 suppression agent to inhibit or reduce cancer cell growth.

The STIP1 suppression agent may be a STIP1 antibody or an antibody against the full-length human STI1 protein (SEQ ID NO:3) or an antibody against a partial sequence. Non limiting examples of STIP1 antibody include, STIP1 MaxPab mouse polyclonal antibody which is available from Abnova Biotechnology Inc., (Taipei City, Taiwan), or monoclonal STIP1 antibody which is commercially available from Sigma-Aldrich (Switzerland). The STIP1 suppression agent can also be a small interfering RNA (e.g, siRNA, short interfering RNA or silencing RNA) targeting STIP1 RNA transcripts to decrease the expression of STIP1. For example, the STIP1 suppression agent can be a biosynthetic precursor of a STIP1 targeted small interfering RNA. Small interfering RNAs are typically short (e.g., about 21 nucleotides in length) double-stranded RNA species with phosphorylated 5' ends and hydroxylated 3' ends with two overhanging nucleotides. The STIP1 suppression agent can be any RNA species, including, but not limited to, microRNA (miRNA), short hairpin RNA, endoribonuclease-prepared siRNA (esiRNA), natural antisense short interfering RNA (natsiRNA), where the RNA species targets STIP1 RNA to decrease the expression of STIP1 in the cell(s).

In yet another embodiment, the invention discloses methods of reducing or inhibiting cancer cell growth in a subject comprising administering an antibody or an antigen-binding portion, which binds to an amino acid sequence at least 90% homologous to SEQ ID NO:1

The cancer may be any solid or hematological tumor, such as, for example, ovarian, endometrial, nasopharyngeal carcinoma, liver, breast, lung, gastric, pancreatic, colon, leukemias, lymphomas, CNS tumors, such as glioblastomas, or a sarcoma. In one embodiment, the cancer is can be pancreatic cancer, endometrial cancer, lung cancer, nasopharyngeal carcinoma, breast cancer and colon cancer. Alternatively, in another embodiment, the subject is substantially free of ovarian cancer.

Treatment with the antibody or the antigen binding fragment thereof and/or the isolated polypeptide described herein may be administered alone, or as an adjuvant to surgery, cryotherapy or radiation therapy, e.g., before surgery to reduce the tumor size and/or following surgery to reduce the possibility of recurrences and metastases, e.g., by inhibition of the growth and migration of circulating tumor cells through the blood stream.

Treatment can be administered before, after or simultaneously with an anti-cancer agent.

The anti-cancer agent includes conventional chemotherapeutic agent, target cancer therapy or radiation therapy. In certain instances, the treatment includes a combination of various anti-cancer agents.

The dosage of the antibody or antigen binding fragment binding to an amino acid sequence at least 90% homologous to SEQ ID NO:1, or the isolated polypeptide comprising an amino acid sequence at least 90% homologous to SEQ ID NO:1 can be determined by a skilled person in the art, which varies in accordance with the age, weight, and condition of the subject to be treated, without undue experimentation.

The antibody or antigen binding fragment which binds to an amino acid sequence at least 90% homologous to SEQ ID NO:1, or the isolated polypeptide comprising an amino acid sequence at least 90% homologous to SEQ ID NO:1 can be administered by any suitable routes including intracranial, intracerebral, intraventricular, intrathecal, intraspinal, oral, topical, rectal, transdermal, subcutaneous, intravenous, intramuscular intranasal, intraperitoneum, intratumor and the like, and can be encapsulated in a carrying agent such as liposome.

Antibody

As used herein, the term "antibody" includes polyclonal, monoclonal, chimeric, humanized, Fv, Fab and F(ab')$_2$; bifunctional hybrid (e.g., Lanzavecchia et al., Eur. J. Immunol. 17:105, 1987), single-chain (Huston et al., Proc. Natl. Acad. Sci. USA 85:5879, 1988; Bird et al., Science 242:423, 1988); and antibodies with altered constant regions (e.g., U.S. Pat. No. 5,624,821).

A monoclonal antibody is a single molecular species of antibody, whereas a polyclonal antibody, which is produced by injecting an animal (such as a rodent, rabbit or goat) with an antigen, and extracting the serum from the animal. A humanized antibody is a genetically engineered (monoclonal) antibody in which the CDRs from a mouse antibody ("donor antibody", which can also be rat, hamster or other similar species) are grafted onto a human antibody ("acceptor antibody"). Humanized antibodies can also be made with less than the complete CDRs from a mouse antibody. Thus, a humanized antibody is an antibody having CDRs from a donor antibody and variable region framework and constant regions from a human antibody. Typically, a humanized antibody comprises (i) a light chain comprising three CDRs from a mouse antibody, a variable region framework from a human antibody, and a human constant region, and (ii) a heavy chain comprising three CDRs from a mouse antibody, a variable region framework from a human antibody and a human constant region. A chimeric antibody is an antibody in which the variable region of a mouse (or other rodent) antibody is combined with the constant region of a human antibody; their construction by means of genetic engineering is well-known in the art (see e.g., Imai et al., Comparing antibody and small molecule therapies for Cancer. Nature Reviews Cancer 6:714-727 (2006); see also, BioAtla, 11011 Torreyana Road, San Diego, California 92121)). Such antibodies retain the binding specificity of the mouse antibody, while being about two-thirds human. The proportion of nonhuman sequence present in mouse, chimeric and humanized antibodies suggests that the immunogenicity of chimeric antibodies is intermediate between mouse and humanized antibodies. Other types of genetically engineered antibodies that may have reduced immunogenicity relative to mouse antibodies, include human antibodies made using phage display methods (Dower et al., WO91/17271; McCafferty et al., WO92/001047; Winter, WO92/20791; and Winter, FEBS Lett. 23:92, 1998, each of which is incorporated herein by reference) or using transgenic animals (Lonberg et al., WO93/12227; Kucherlapati WO91/10741, each of which is incorporated herein by reference).

The antibody of the invention is typically substantially purified away from undesired contaminants. This means the antibody is typically at least about 50% w/w (weight/weight) pure, as well as being substantially free from interfering proteins and contaminants. Preferably the antibody is 91, 92, 93, 9, 95, 96, 97, 98, or 99% w/w pure.

An antibody or an antigen binding fragment that binds to an amino acid sequence is at least 90% homologous to SEQ ID NO:1 is said to inhibit one or more biological activities of STIP1, such as SMAD1/SMAD5 phosphorylation, ERK1/ERK2 phosphorylation, ID3 gene expression activation, stimulate DNA synthesis stimulation and cell proliferation.

An antibody or an antigen binding fragment thereof that binds to an amino acid sequence at least 90% homologous to SEQ ID NO:1 includes antibodies in their natural tetrameric form (2 light chains and 2 heavy chains) and may be of any of the known isotypes, i.e., IgG, IgA, IgM, IgD and IgE as well as their subtypes, i.e., human IgG1, IgG2, IgG3, IgG4 and mouse IgG1, IgG2a, IgG2b, and IgG3. In another embodiment, the antibody or the antigen binding portion binds an amino acid sequence at least 90%, 91%, 92%, 93%, 94%, 95%, 96%, 97%, 98%, 99% or 100% homologous to SEQ ID NO:1.

The antibodies of the present invention can be recovered from a subject, such as human, by selecting one or more B cells that produces one or more antibodies against SEQ ID NO:1, and recovering said antibodies from the B cells. Mouse antibodies against SEQ ID NO:1 are made by standard methods well-known in the art. In one embodiment, the steps of making an antibody which binds to an amino acid sequence at least 90% homologous to SEQ ID NO:1 include: immunizing a subject, such as an animal, with a peptide having an amino acid sequence comprising SEQ ID NO:1 in an appropriate adjuvant intraperitoneally, intravenously, or subcutaneously into the footpad, followed by extraction of spleen or lymph node cells of the animal, followed by fusion with a suitable immortalized cell line for formation of hybridoma(s), and then selecting the hybridoma(s) that produce antibody binding to amino acid sequence at least 90% homologous to SEQ ID NO:1. The immunized animal can be any animal that is capable of producing recoverable antibodies when administered an immunogen, such as, but not limited to, rabbits, mice, rats, hamsters, goats, horses, monkeys, baboons and humans. After the host is immunized and the antibody against SEQ ID NO:1 is produced, the antibody is assayed to confirm that they are specific for the antigen of interest and to determine whether they exhibit any cross reactivity with any other antigens. One method of conducting such assays is a sera screen assay as described in U.S. Patent Publication No. 2004/0126829. Antibody against SEQ ID NO:1 can be characterized for binding to the polypeptide antigen (e.g., SEQ ID NO:1) by a variety of known techniques. For example, in an ELISA, microtiter plates are coated with the toxin or toxoid antigen in PBS, and then blocked with irrelevant proteins such as bovine serum albumin (BSA) diluted in PBS. Dilutions of plasma from toxin-immunized mice are added to each well and incubated. The plates are washed and then incubated with a secondary antibody conjugated to an enzyme (e.g., alkaline phosphatase). After washing, the plates are developed with the enzyme's substrate (e.g., ABTS), and analyzed at a specific OD. In other embodiments, to determine if the selected monoclonal antibodies bind to the polypeptide antigen (e.g., SEQ ID NO:1), the antibody can be biotinylated and the labeled antibodies detected with a streptavidin labeled probe. The antibodies can be tested for reactivity with the polypeptide antigen (e.g., SEQ ID NO:1) by Western blotting.

The antibodies which bind to an amino acid sequence at least 90% homologous to SEQ ID NO:1 can also be made by phage display or transgenic mice methods well-known in the arts. In one aspect, the host is transgenic and produces human antibodies, e.g., a mouse expressing the human immunoglobulin gene segments. U.S. Pat. Nos. 8,236,311; 7,625,559 and 5,770,429, the disclosure of each of which is incorporated herein by reference in its entirety. Lonberg et al., Nature 368(6474): 856-859, 1994. Lonberg, N., Handbook of Experimental Pharmacology 113:49-101, 1994. Lonberg, N. and Huszar, D., Intern. Rev. Immunol., 13: 65-93, 1995. Harding, F. and Lonberg, N., Ann. N.Y. Acad. Sci., 764:536-546, 1995. In one embodiment, the antibody can be made by the following steps: immunizing a subject with a polypeptide comprising SEQ ID NO:1; recovering mRNA from a B cells of said subject; converting said recovered mRNA to cDNA; expressing said cDNA in phages such that an antibody encoded by said cDNA are then presented on the surface of said phages; selecting phages that present said antibody; recovering nucleic acid molecules from said selected phages that encode said antibody; expressing said recovered nucleic acid molecules in a host cell; and recovering antibody from said host cell that binds an amino acid sequence comprising SEQ ID NO:1.

Genetically engineered antibody against SEQ ID NO:1, e.g., chimeric antibody, may be expressed by a variety of well known art-known methods. For example, genes encoding their light and heavy chain V regions may be synthesized from overlapping oligonucleotides and inserted together with available C regions into expression vectors (e.g., commercially available from Invitrogen) that provide the necessary regulatory regions, e.g., promoters, enhancers, polyA sites, etc. Use of the CMV promoter-enhancer is preferred. The expression vectors may then be transfected using various well-known methods such as lipofection or electroporation into a variety of mammalian cell lines such as CHO or non-producing myelomas including Sp2/0 and NSO, and cells expressing the antibodies selected by appropriate antibiotic selection. See, e.g., U.S. Pat. No. 5,530,101. Larger amounts of antibody may be produced by growing the cells in commercially available bioreactors.

Once expressed, the antibody against SEQ ID NO:1 may be purified according to standard procedures of the art such as microfiltration, ultrafiltration, protein A or G affinity chromatography, size exclusion chromatography, anion exchange chromatography, cation exchange chromatography and/or other forms of affinity chromatography based on organic dyes or the like.

Pharmaceutical Composition

In one aspect, the present invention provides pharmaceutical composition comprising an isolated polypeptide comprising an amino acid sequence at least 90% homologous to SEQ ID NO:1 and a pharmaceutically acceptable carrier. In another embodiment, the pharmaceutical composition further comprises an antibody against the full-length human STIP1 protein (SEQ ID NO:3).

The isolated polypeptides of the pharmaceutical composition are at least 90, 91, 92, 93, 94, 95, 96, 97, 98, 99 or 100% homologous to the amino acid sequence of SEQ ID NO:1.

In one embodiment, the isolated polypeptide of the pharmaceutical composition differs from SEQ ID NO:1 by a small number of functionally inconsequential, amino acid substitutions (e.g., conservative substitutions), deletions, or insertions, while retaining the functional properties of SEQ ID NO:1, i.e., such polypeptide inhibits the cancer cell growth in at least one, and preferably all, in vitro or in vivo assays described herein. For purposes of classifying amino acids substitutions as conservative or nonconservative, amino acids may be grouped as follows: Group I (hydrophobic side chains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another.

In one embodiment, the isolated polypeptide differs from SEQ ID NO:1 by up to 5 amino acids change, such as 1, 2, 3, 4, or 5 amino acids change.

The present invention also discloses pharmaceutical compositions comprising an antibody or antigen binding fragment which binds to a peptide having an amino acid sequence at least 90% homologous to SEQ ID NO:1.

The pharmaceutical compositions may further comprise a signal peptide that facilitates the entry into the cell (Horibe et al. J Translation Med 9:8, 2011), physiologically acceptable carrier, optionally with excipients or stabilizers, in the form of lyophilized or aqueous solutions. Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids, carbohydrates, chelating agents, sugars, and other standard ingredients known to those skilled in the art.

The pharmaceutical compositions of the present invention can be prepared as injectables, either as liquid solutions or suspensions, or as solid forms which are suitable for solution or suspension in liquid vehicles prior to injection. The pharmaceutical composition can also be prepared in solid form, emulsified or the active ingredient encapsulated in liposome vehicles or other particulate carriers used for sustained delivery. For example, the pharmaceutical composition can be in the form of an oil emulsion, water-in-oil emulsion, water-in-oil-in-water emulsion, site-specific emulsion, long-residence emulsion, stickyemulsion, microemulsion, nanoemulsion, liposome, microparticle, microsphere, nanosphere, nanoparticle and various natural or synthetic polymers, such as nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures, that allow for sustained release of the pharmaceutical composition.

The following examples further illustrate the present invention. These examples are intended merely to be illustrative of the present invention and are not to be construed as being limiting.

Material and Methods

1. Preparation of Cell Culture

Human ovarian cancer cell lines TOV112D, TOV21G, SKOV3, MDAH2774, ES2, MDAH2774,BG1; human endometrial cancer cell line RL95-2, human pancreatic cancer cell line BxPC3, breast cancer cell line (MCF7) and colon cancer cell line (HT29) were obtained from ATCC (Rockville, Md., USA). Lung cancer cell line CL1-0 and nasopharyngeal carcinoma cell line NPC-BM1 were obtained from Dr. CC Wu (Department of Medical Biotechnology and Laboratory Science, Chang-Gung University, Taoyuan, Taiwan), Wu et al. Mol. Cell Proteomics 9(6): 11100 (20101). Mouse ovarian cancer cell line MOSEC was obtained from Dr. CL Chang (Department of Obstetrics and Gynecology, Mackay Memorial Hospital, Taipei, Taiwan), Chang et al. Cancer Research 67:10047 (2007). TOV112D, TOV21G, SKOV3, MDAH2774, ES2 and RL95-2 were cultured in Dulbecco's modified Eagle's medium/F-12 supplemented with 10% fetal bovine serum and antibiotics at 37° C. in 5% CO2 humidified atmosphere. BxPC3, CL1-0, NPC-BM1 and MOSEC cells were cultured in RPMI 1640 media supplemented with 10% fetal bovine serum.

2. Proteomics Analysis of Secreted Proteins from Cancer Cell Lines

The procedures for identifying secreted protein of various cancer cell lines were previously reported (Wu et al 2010). Briefly, cancer cells were grown to confluence in 15-cm culture dishes. The cancer cells were washed and incubated with serum-free media for 24 h. The supernatants were harvested and centrifuged to remove cell contaminants. Proteomics analysis was performed with one-dimensional SDS-PAGE, in-gel protein digestion, followed by reverse-phase liquid chromatography/tandem mass spectrometry (LC/MS-MS). Protein identification was performed using the open source TPP software (version 3.3), the SEQUEST search, the PeptideProphet program and the ProteinProphet program.

3. Antibody Transfection

Cancer cells were transfected with an STIP1 antibody in PLUSin reagent (Polyplus-transfection Inc., NY, USA) according to manufacturer's protocol. In summary, $2\times10^3 \sim 6\times10^3$ cancer cells were seeded in a 96-well plate overnight, followed by PBS rinse and the addition of 180 µl of OPTI-MEM. 0.6 µg of mouse STIP1 antibody were diluted in 20 mM HEPES, mixed with 1.2 µl of PLUSin by vortexing, followed by incubation at room temperature for 15 min. The antibody/PLUSin mixture was added to the cancer cells by gentle swirling the plate. The STIP1 antibody and the control IgG used in the working examples described herein are commercially available from Abnova Biotechnology Inc., (Taipei City, Taiwan). The STIP1 antibody in the working examples described herein can be used to detect recombinant full length STIP 1 (SEQ ID NO:3).

4. Cell Migration Assays

BG1 and MDAH2774 cells ($10^6$/well) treated with either rhSTIP1 (400 nM) or void STIP1 were cultured in serum free medium for 24 h before plated in the upper chamber of the 8-µm pore (24-well) transwell insert (Corning and Transwell, N.Y., USA). The lower chamber was filled with 800 µl of DMEM/F12 media and 0.5 µg/ml of fibronection (Sigma, USA). After 26 h of incubation, the cells that had migrated through the pores and reattached to the lower chamber were stained with fluorescein calcein-AM (4 µg/ml) (BD, USA). The number of viable cells that had traversed the filter was determined by the fluorescence of each sample in a Tecan Infinite M200 Multiwell reader (Tecan, Switzerland). Neutralization of STIP1 was performed using STIP1 antibody (800 nM). Each cell migration assay was repeated in three separate occasions.

6. Cell Viability Assay $1\sim2\times10^4$ Cancer cells were plated per well in 96-well plates overnight, then transfected with a mouse STIP1 antibody (commercially available from Abnova Biotechnology Inc.) for 48 h before they were assessed. The inhibitory effect of the STIP1 antibody on the cancer cells was measured by the MTT [3-(4,5-Dimethylthiazol-2-yl)-2,5-Diphenyltetrazolium Bromide] method (Sigma St. Louis, Mo.).

The optical density was measured at 570 nm using an automated scanning multiwell spectrophotometer (Wallac Victor2 spectrophotometer; PerkinElmer, Boston, Mass., USA).

7. Western Blot Analysis

Cell lysates were prepared with a RIPA buffer (150 mM NaCl, 20mM Tris-Cl pH7.5, 1% Triton X-100, 1% NP40, 0.1% SDS, 0.5% deoxycholate) containing freshly added proteinase and phosphatase inhibitors (Bionovas, Toronto). Protein concentration was measured using the Bradford method. Fifty μg of each sample was electrophoresed in 10% SDS-polyacrylamide gels, and transferred to nitrocellulose membranes. STIP1 antibody was commercially available from Abnova Biotechnology and Santa Cruz Biotechnology, Santa Cruz, Calif., actin was commercially available from Sigma, the corresponding horseradish peroxidase-conjugated antibody was commercially available from Santa Cruz Biotechnology, enhanced chemiluminescence reagent was commercially available from Millipore Inc. (Millipore, Billerica, Mass.). The signal intensity of autoradiogram was quantified using the UN-SCAN-IT software (Silk Scientific, Orem, Utah), and relative intensity of each sample was normalized by the corresponding actin intensity. For antibody neutralization assay, cancer cells were cultured in serum-free medium for 24 h, and treated with rhSTIP1 for another 24 h in the presence or absence of the STIP1 monoclonal antibody, which were pre-incubated at 37° C. for 1 h. Endogenous phospho-SMAD1/5 was detected with western blot analysis.

8. Immunohistochemistry (IHC)

Paraffin-embedded ovarian cancer tissues were sectioned to 4 μm, then deparaffinized with xylene, and rehydrated with ethanol solutions. Ovarian cancer tissue sections were stained with a control mouse IgG or an STIP1 antibody (Abnova, Taipei City, Taiwan), in an automated IHC stainer with Ventana Basic DAB (3,3'-diaminobenzidine) Detection Kit (Tucson, Ariz.). Hematoxylin was used for counterstaining To quantify immunointensity of each IHC slide, histoscore was calculated by multiplying % of cancer cells (0~100%) with immunointensity (0~3), as previously described (Chao et al 2010, Chao et al 2012). Commercially available tissue arrays (FDA-805-1 and 2, Biomax Inc., USA) were used to detect tissue distribution of STIP1 in various human organs and corresponding cancers.

9. Immunofluorescent Microscopy

Cancer cells were cultured on cover slides at a concentration of $3 \times 10^5$ cells/well in 6-well plates overnight, followed by serum starvation for another 24 h. After transfecting with STIP1 antibody for 72 h, cancer cells were fixed with 2% of paraformaldehyde at 4° C. for 30 min, and incubated in blocking buffer (5% normal goat serum in PBS) for 1 h at room temperature, to reduce non-specific binding. Cancer cells were incubated with an anti-mouse Alexa Fluor-488 (Invitrogen, 1:100) for detecting the STIP1 antibody and the rabbit polyclonal anti-cleaved caspase 3 antibody (Cell Signaling Technology, Beverly, Mass., USA, 1:100). After incubation with an anti-rabbit Alexa Fluor-546 (1:100, Invitrogen, Carlsbad, Calif.), the slides were mounted with Vectashield mounting medium (Vector Laboratories, Burlingame, Calif.), and analyzed under the Leica TCS SP2 laser scanning confocal system (Leica Inc., Germany).

10. BrdU Proliferation Assay and Ki67 Immunocytochemistry

The BrdU assay and Ki67 staining procedures have been reported previously (Tsai et al 2012, Wang et al 2010). For BrdU assays, cancer cells were seeded at a density of $10^4$ cells/well in a 96-well plate overnight, and cultured in serum-free medium for 24 h. Cancer cells were treated with 0.4 μM of rhSTIP1 in the presence of BrdU for 24 h. DNA synthesis activity was measured using BrdU ELISA kit (Roche Applied Science). For immunocytochemistry studies of Ki-67, MDAH2774 cells were cultured on Lab-Tek II chamber slides (Nalge Nunc International, Denmark) overnight. After serum starvation or RNAi transfection for 72 h, cancer cells were treated with 0.4 μM of STIP1 with or without an STIP1 antibody for another 24 h. The slides were fixed with 99.9% of ethanol, rehydrated with PBS, treated with 3% of hydrogen peroxide for 20 min, permeabilized with 0.1% Triton X-100 (Sigma) for 15 min, and stained with anti-Ki67 antibody (Thermo Fisher Scientific, Rockford, Ill.).

11. Cell Cytotoxicity Assays

Cells were seeded at $1 \sim 2 \times 10^4$ cell per well of 96-well plates and transfected with the STIP1 antibody at 37° C. for 48 hours. To assay the activity of lactate dehydrogenase (LDH), 100 pl of a reaction mixture (Cytotoxicity Detection Kit PLUS®, Roche, Basel, Switzerland) and the conditional medium were added to each well and incubated in the dark for 5-20 min. The water-soluble formazan dye displayed a broad absorption maximum at approximately 500 nm in the Victor2 ELISA reader. The Cell Death Detection ELISA photometric enzyme immunoassay (Roche) was used for in vitro quantitative determination of cytoplasmic histone-associated DNA fragments (mono- and oligonucleosomes) as an indicator of apoptosis. The absorbance was measured at 405 nm.

12. In Vivo Animal Model

Five-week-old female C57BL/6 mice were obtained from the National Animal Center, Taiwan, and had free access to water and food during the trial. All of the procedures carried out in the animal study were approved by the Institutional Animal Care and Use Committee of the Chang Gung Memorial Hospital, Taiwan. All of the experiments were conformed to the Guide for the Care and Use of Laboratory Animals published by the US National Institutes of Health (NIH Publication No.85-23, revised 1996).

13. Tumor Growth Monitoring Using an In Vivo Imaging System

Mouse ovarian surface epithelial cancer cells that expressed luciferase (MOSEC/LUC) were suspended in Hanks' balanced salt solution (HBSS). Each mouse was injected with $10^6$ of MOSEC cells intraperitoneally, using a 23 gauge needle (Becton Dickson, Franklin Lakes, N.J., USA). Each mouse was injected with luciferin intraperitoneally (100 μl of 0.4 mg/mL luciferin, Promega) the following day and imaged with an IVIS imaging system (Xenogen Corp., Alameda, Calif., USA) 10 min after the injection. All mice were sedated with isoflurane and imaged at the Molecular Imaging Core Laboratory of Chang Gung Memorial Hospital, Taiwan. Light outputs were quantified using the LivingImage software (Xenogen Corp.). Raw values were reported as photons/second/cm2/sr.

Results

Detection of STIP1 in Multiple Human Cancers

As illustrated in FIG. 1, ovarian cancer tissue has a much higher STIP1 histoscore (over 200) than that of normal ovarian tissue (0). Several other cancers also had elevated STIP1 histoscore compare to their corresponding normal tissue, including brain cancer, endometrial cancer, thyroid cancer, lung cancer, stomach cancer, liver cancer, prostate cancer, colon cancer, and skin cancer.

FIG. 2 shows that various STIP1 polypeptides were expressed in nasopharyngeal cancer (NPC-TWO4), lung cancer (CL1-5), and liver cancer (Hep3B) cells.

STIP1 Antibody Reduced Cancer Cell Viability and Induced Cancer Cell Death

The following cancer cell lines were transfected using the PLUSin reagent with STIP1 antibodies to block endogenous STIP1: MDAH2774 (ovarian cancer), RL95-2 (endometrial cancer), NPC-BM1 (nasopharyngeal cancer), BxPC3 (pancreatic cancer), CL1-0 (lung cancer), HT29 (colon cancer), and MCF7 (breast cancer) cells. Cancer cell viability was assessed using the MTT assay, while cell death was assessed using LDH assay.

Figure 3:
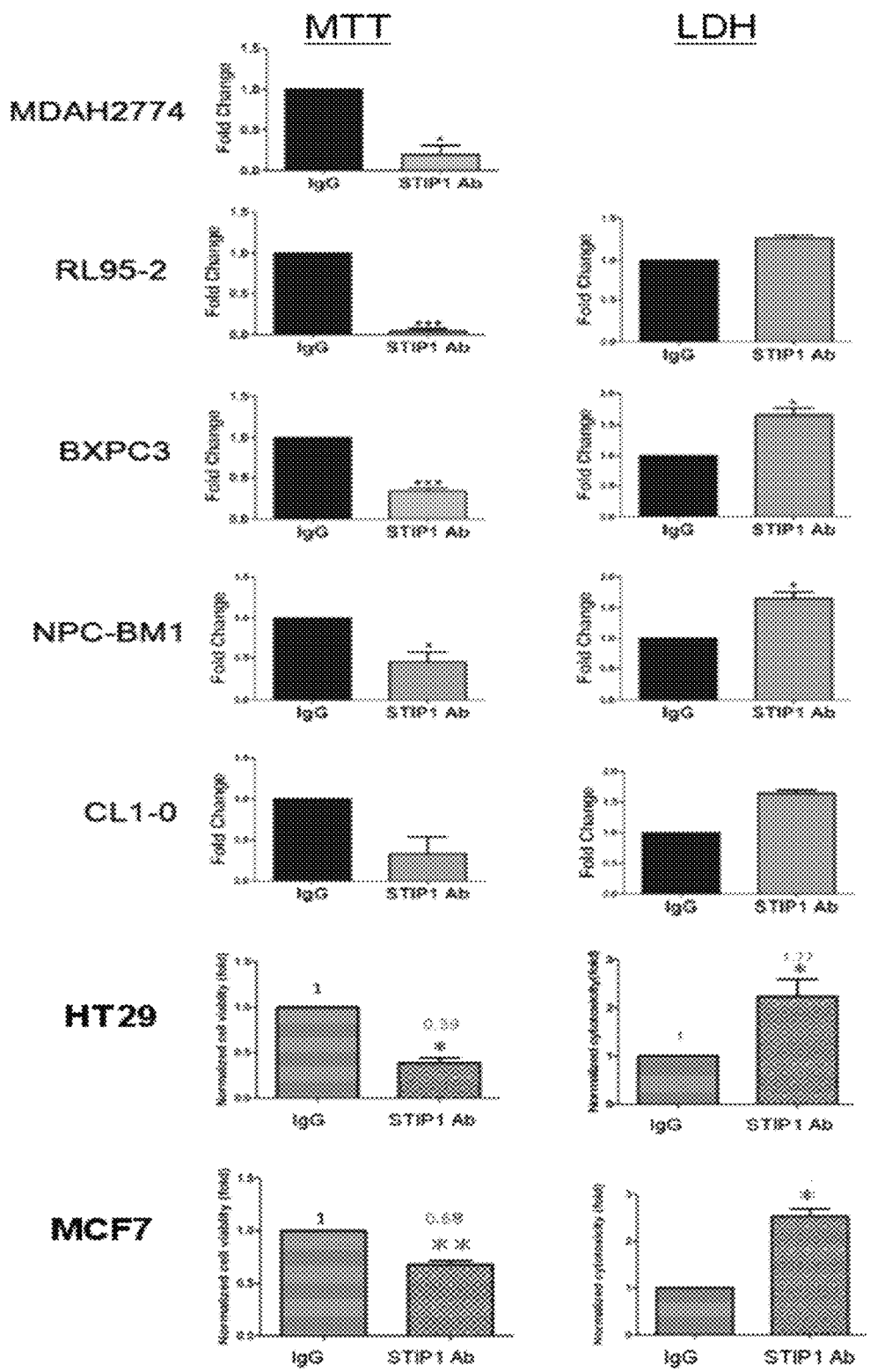
FIG. 3 illustrates the cytotoxic effects of STIP1 antibody in ovarian cancer cells (MDAH2774), endometrial cancer cells (RL95-2), pancreatic cancer cells (BXPC3), nasopharyngeal cancer cells (NPC-BM1), lung cancer cells (CL1-0), colon cancer cells (HT29), and breast cancer cells (MCF7).

FIGS. 3 shows that in all of the tested cancer cell lines, STIP1 antibody transfection led to a lower MTT level (less cell viability) and a higher LDH level (more cell death).

Figure 4:
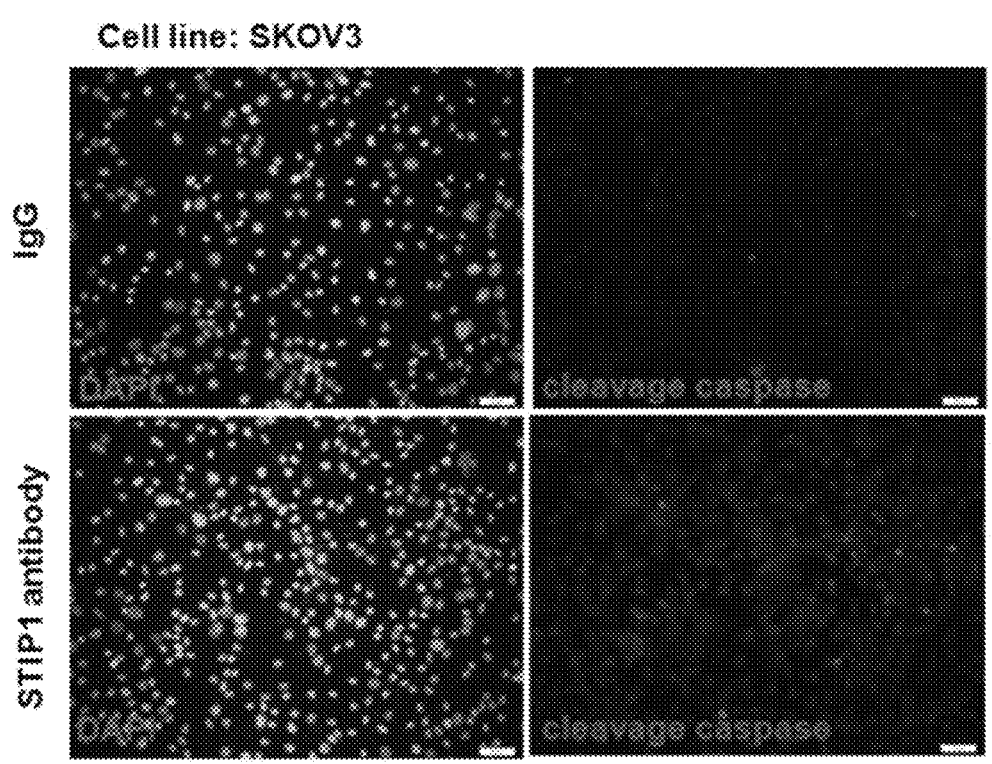
FIG. 4 illustrates the cleaved caspase 3 level in STIP1 antibody-transfected SKOV3 cells (lower panel) and control IgG-transfected SKOV3 cells (upper panel).

Caspase 3 cleavage is also used as an indicator for cell death. After the ovarian cancer cells (SKOV3) was transfected with the STIP1 antibody, cleaved caspase 3 level was assessed using immunoflorescent microscopy. In FIG. 4, ovarian cancer cells transfected with an STIP1 antibody have a higher level of cleaved caspase-3 (lower right panel in FIG. 4) than those cancer cells transfected with a control IgG (upper right panel in FIG. 4).

These results indicate that STIP1 antibody is effective in inhibiting cancer cell growth.

Figure 5A:
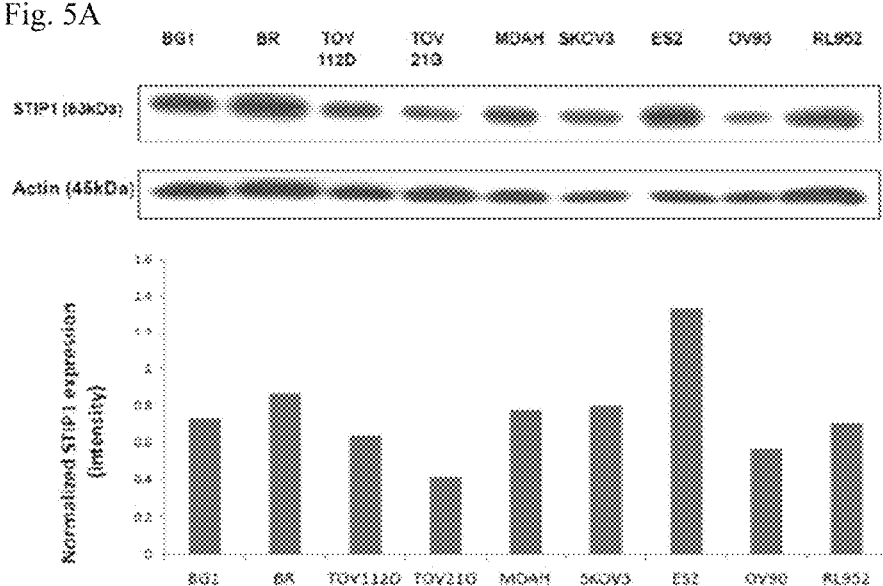
FIG. 5A illustrates the endogenous STIP1 level in various ovarian cancer cell lines (BG1, BR, TOV112D, TOV21G, MDAH2774, SKOV3, ES2 and OV90) and in an endometrial cancer cell line (RL95-2).

FIG. 5A shows endogenous STIP1 expression level in eight ovarian cancer cell lines and one endometrial cancer cell line (RL95-2. Among these cell lines, the highest endogenous STIP1 expression was in ES2 cell line and the lowest was in TOV21G cell line. Based on these results, ES2 and TOV21G cell lines were among the most suitable candidates for testing the effects and the specificity STIP1 antibodies in vitro.

Figure 5B:
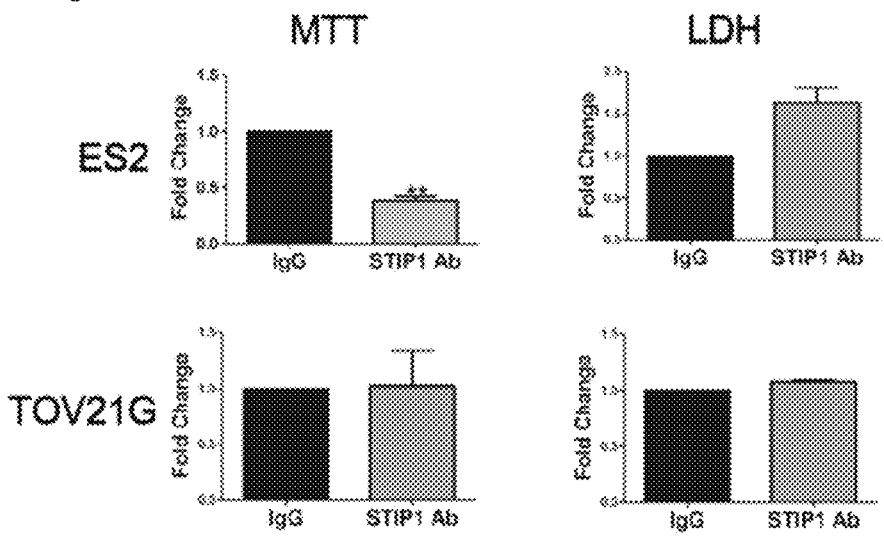
FIG. 5B illustrates the cytotoxic effect of STIP1 antibody as compared with a control IgG in an ES2 cell line and TOV21G cell line.

Following STIP1 antibody transfection, ES2 cell line (with highest endogenous STIP1 expression) showed a lower MTT level (less cell viability) and a higher LDH level (more cell death) than TOV21G cells (with lowest endogenous STIP1-expression). See FIG. 5B. Since both ES2 cells and TOV21G cells are clear cell ovarian cancer cells, the different cytotoxic effect of STIP1 antibody was due to different STIP1 expression level, rather than the different cancer type.

Figure 6A:
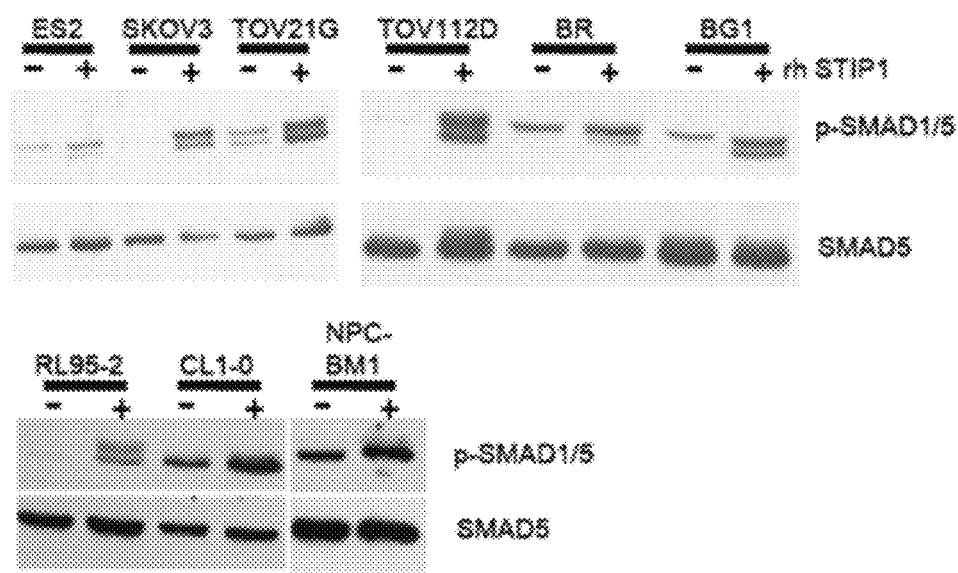
FIG. 6A illustrates the SMAD1/5 phosphorylation effect of recombinant human STIP1 protein (rh STIP1) on various cancer cell lines.

STIP1 Antibody Neutralizes the Effects of Secreted STIP1 on Signal Induction, Cell Proliferation and Migration of Cancer Cells Without being bound by any theory, it is believed that STIP1 triggers ALK2-SMAD1/5 phosphorylation pathway and ID3 pathway to promote ovarian cancer cell proliferation. FIG. 6A shows that rhSTIP1 stimulates SMAD1/5 phosphorylation in six ovarian cancer cell lines (ES2, SKOV3, TOV21G, TOV112D, BR and BG1), one endometrial cancer cell line (RL95-2), one lung cancer cell line (CL1-0) and one nasopharyngeal carcinoma cell line (NPC-BM1).

Figure 6B:
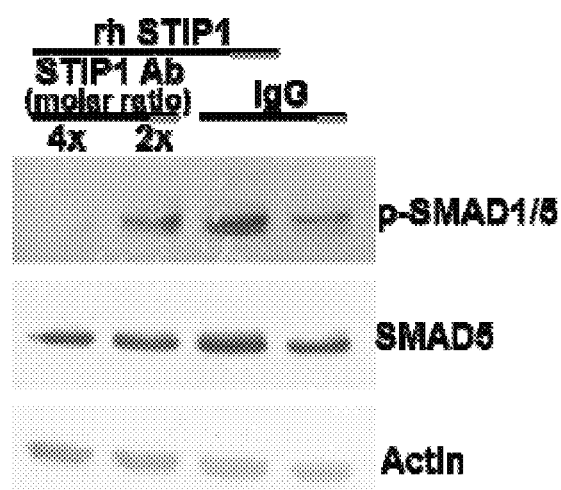
FIG. 6B illustrates the suppression of SMAD1/5 phosphorylation by STIP1 antibody.

STIP1 antibody was administered to verify that SMAD1/5 phosphorylation in FIG. 6A was induced by the interaction between STIP1 and STIP1 cell membrane receptor. FIG. 6B shows that SMAD1/5 phosphorylation was partially suppressed by STIP1 antibody at a molarity ratio of 2:1 (STIP1 antibody:rhSTIP1), and SMAD1/5 phosphorylation was completely suppressed by STIP1 antibody at a molarity ratio of 4:1 (STIP1 antibody:rhSTIP1). These results suggest that STIP1 antibody can neutralize STIP1 secreted by cancer cells.

Figure 6C:
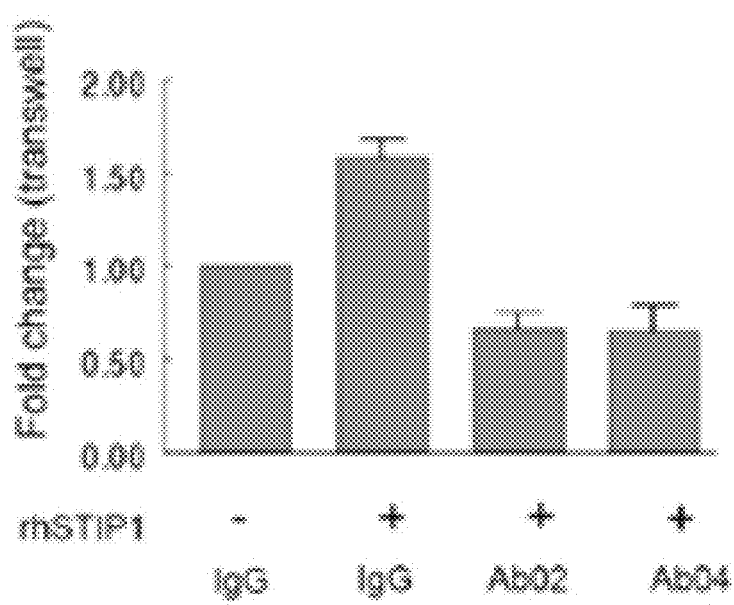
FIG. 6C illustrates the effect of rhSTIP1 and STIP1 antibody on ovarian cancer cell migration.

FIG. 6C shows STIP1 antibody (Ab02 and Ab04) suppressed rhSTIP1-stimulated cell migration.

BrdU is an analogue of thymidine which can replace thymidine during DNA replication, and Ki67 is a nuclear protein that is associated with cell proliferation. BrdU incorporation assay and immunocytochemistry for endogenous Ki67 were used as an index for cell proliferation. Treatment with rhSTIP1 increased the BrdU incorporation rate and Ki67 staining of ovarian cancer cells (FIGS. 7A to FIG. 7F). These activities were reduced by treatment with an ALK2/ALK3 inhibitor (LDN193189) and an ERK inhibitor (PD98059) (FIGS. 7A and 7B), an STIP1 antibody (FIGS. 7C and 7D), and ALK2 siRNA and STIP1 siRNA (FIGS. 7E and 7F). Of note, inhibition of ERK activity by PD98059 strongly inhibited cell proliferation, but even in such inhibition, treatment with rhSTIP1 still significantly stimulated BrdU incorporation (FIG. 7A). These results indicated that ERK pathways are very important for cell proliferation, but the ALK2-SMAD might be more specific for the rhSTIP1-stimulated cell proliferation. Furthermore, knockdown of endogenous STIP 1 alone did not inhibit cell proliferation and neither did it affect the stimulation of cell proliferation by exogenous rhSTIP1 (FIGS. 7E and 7F).

These data further support the use of STIP1 antibody to inhibit proliferation and migration of cancer cells.

In Vivo Evaluation of STIP1 Antibody in Cancer Cell Inhibition

Figure 8A:
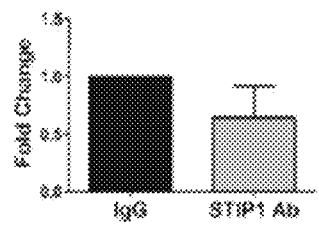
FIG. 8A illustrates the effect of STIP1 antibody on MOSEC cells.
Figure 8B:
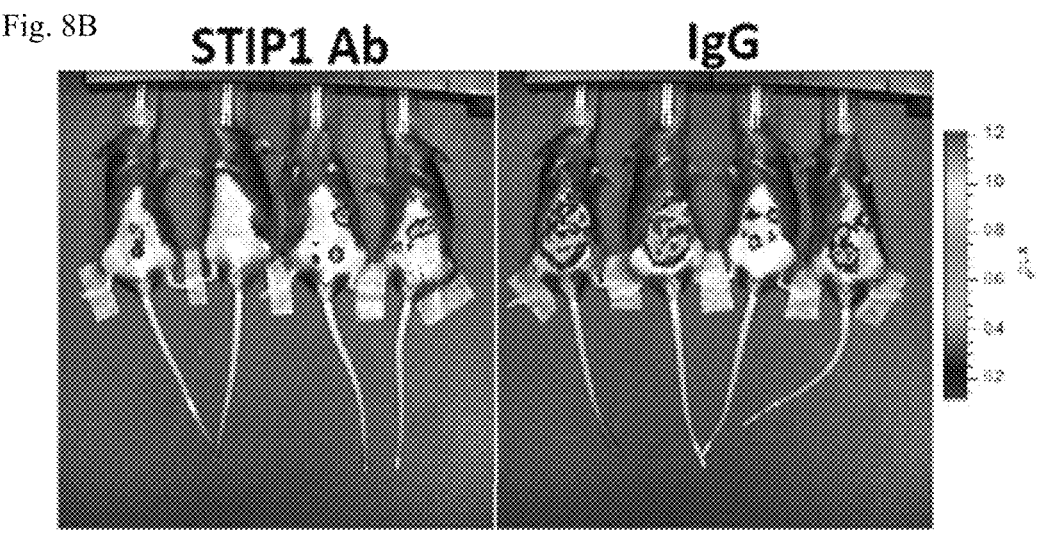
FIG. 8B and FIG. 8C illustrate the change in tumor volume in STIP1 antibody-treated mice as compared with control IgG treated mice.
Figure 8C:
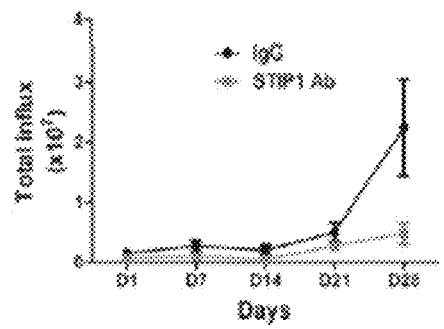
Figure 8D:
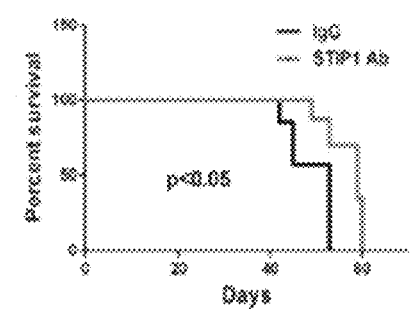
FIG. 8D illustrates the survival time in STIP1 antibody-treated mice as compared with control IgG treated mice.

Mouse Ovarian Surface Epithelial Cells (MOSEC) are sensitive to the cytotoxic effect of STIP1 antibody (see FIG. 8A). $10^6$ of MOSEC cells were inoculated into the abdominal cavity of C57BL/6 mice, followed by the intravenous injection of 100 μg of STIP1 antibody via tail vein twice a week. Tumor growth was assessed 4 weeks later using Xenogen IVIS 200 In Vivo Imaging System (Xenogen Corp., Alameda, Calif., USA). FIGS. 8B and 8C show that mice treated with STIP1 antibody have a lower tumor volume as compared to mice treated with control IgG. FIG. 8D shows that mice treated with STIP1 antibody have a significantly longer survival time (median survival time was 59 days) as compared to mice treated with control IgG (median survival time was 53 days).

These results suggest that STIP1 antibody is effective in cancer cell inhibition and prolongs survival.

STIP1 Epitope For Cancer Cell Inhibition

Figure 9A:
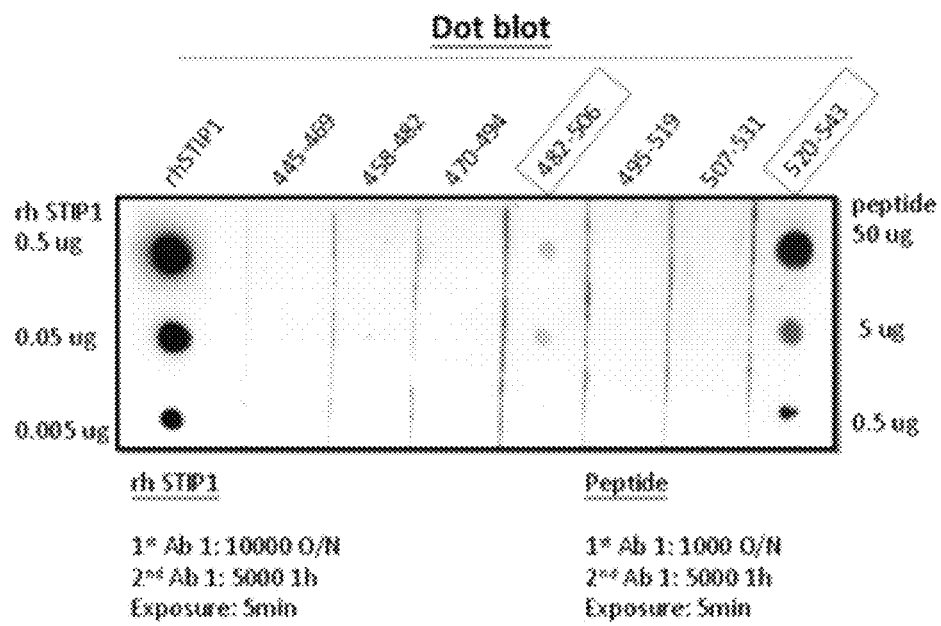
FIG. 9A illustrates the binding affinity of STIP1 antibody to a panel of overlapping STIP1 amino acid (a.a.) sequences, including rhSTIP1 (control), a.a. sequence number 445-469 (SEQ ID NO: 26), 458-482 (SEQ ID NO: 27), 470-494 (SEQ ID NO: 28), 482-506 (SEQ ID NO: 2), 495-519 (SEQ ID NO: 29), 507-531 (SEQ ID NO: 30), and 520-543 (SEQ ID NO: 1).

In FIG. 9A, the following STIP1 polypeptides were dot blotted on a nylon membrane and incubated with an STIP1 antibody: STIP1 polypeptides with amino acid (a.a.) sequence number 445-469, 458-482, 470-494, 482-506 (SEQ ID NO:2), 495-519, 507-531, and 520-543 (SEQ ID NO:1). The entire rhSTIP1 (a.a. sequence number 1 to 543) was used as positive control (the left lane). The data showed the STIP1 polypeptide with a.a. sequence number 520-543 (SEQ ID NO:1) have the highest affinity to STIP1 antibody used in this assay, followed by the STIP1 polypeptide with a.a. sequence number 482-506 (SEQ ID NO:2).

Figure 9B:
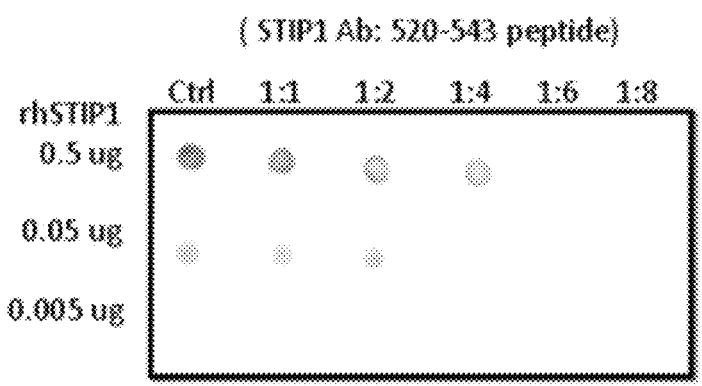
FIG. 9B illustrates the neutralizing effect of various concentrations of STIP1 polypeptide 520-543 (peptide 520) on STIP1 antibody.

The entire rhSTIP1 at different concentrations were dot blotted on a nylon membrane, and incubated with STIP1 antibody. The STIP1 antibody was pre-incubated with STIP1 polypeptide 520-543 (SEQ ID NO:1), at various antibody/polypeptide concentration ratios (from 1:1 to 1:8). FIG. 9B shows that STIP1 polypeptide 520-543 (SEQ ID NO:1) neutralized the binding of STIP1 antibody to rhSTIP1 in a dose dependent fashion. This result further suggests that STIP1 epitope for cancer cell inhibition is located at STIP1 a.a. sequence number 520 to 543 (SEQ ID NO:1).

STIP1 Polypeptide 520-543 (SEQ ID NO:1) Suppresses Cancer Cells

Figure 10A:
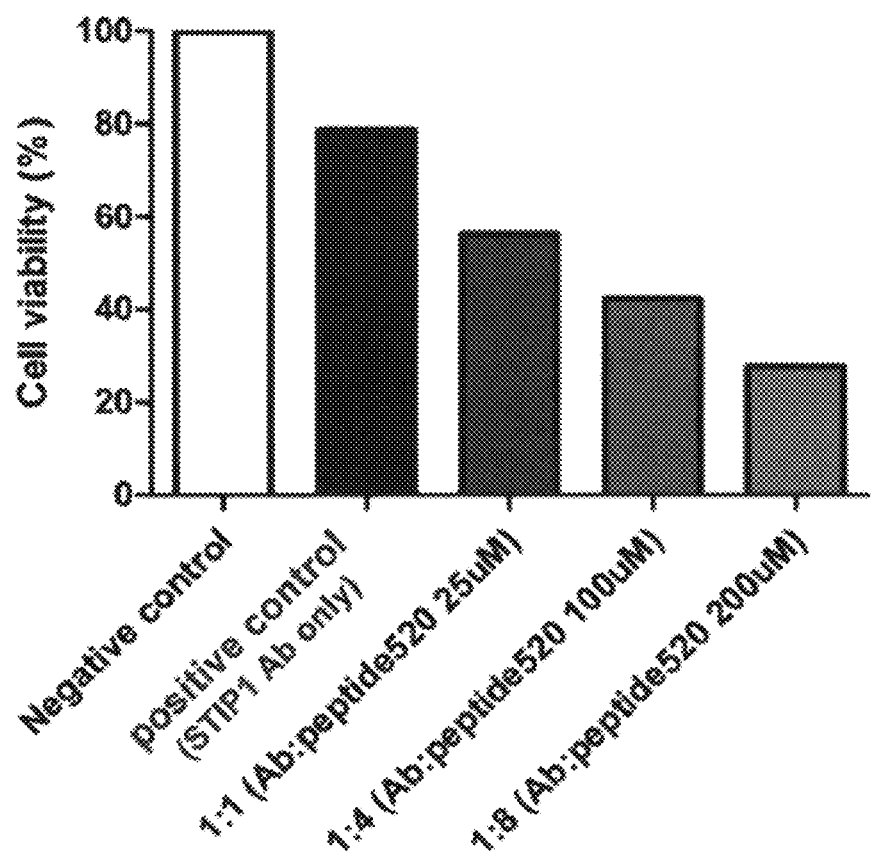
FIG. 10A illustrates cancer cell (MDAH2774) viability in group treated with STIP1 antibody alone, and groups treated with the combination of STIP1 antibody and various concentrations of STIP1 polypeptide 520-543 (SEQ ID NO:1).

Given the neutralizing effect of STIP1 polypeptide 520-543 (SEQ ID NO:1) on STIP1 antibody, co-transfecting STIP1 antibody and STIP1 polypeptide 520-543 in cancer cells may reduce the suppression effect of STIP1 antibody. FIG. 10A and Table 1 show cell viability of ovarian cancer cells (MDAH2774) transfected with STIP1 antibody only (positive control) and STIP1 antibody with various concentrations of STIP1 polypeptide 520-543. Cell viability was evaluated using MTT assays. Unexpectedly, co-transfection of an STIP1 antibody and STIP1 peptide 520-543 in cancer cells showed synergistic suppression of cell viability than the transfection of STIP1 antibody alone. For example, the cell viability for STIP1 antibody was 78.81% (Table 1), the cell viability for 25 uM of STIP1 polypeptide 520-543 was 102% (Table 2), and the cell viability for STIP1 antibody and 25 uM of STIP1 polypeptide 520-543 was 56.38% (Table 1). Similarly, the cell viability for 200 uM of STIP1 polypeptide 520-543 was 28.64% (Table 2), and the cell viability for STIP1 antibody and 25 uM of STIP1 polypeptide 520-543 was 27.67% (Table 1).

TABLE 1

Cell Viability of ovarian cancer cells (MDAH2774) transfected with STIP1 antibody only (positive control) and STIP1 antibody with various concentrations of STIP1 polypeptide 520-543.

|  | Negative control | Positive control (STIP1 Ab only) | 1:1 (Ab:peptide) | 1:4 (Ab:peptide) | 1:8 (Ab:peptide) |
|---|---|---|---|---|---|
| Original O.D | 1.06 | 0.83 | 0.60 | 0.45 | 0.29 |
| Normalized O.D | 1 | 0.78 | 0.56 | 0.42 | 0.28 |
| Cell viability (%) | 100 | 78.82 | 56.38 | 42.19 | 27.67 |

TABLE 2

Cell Viability of ovarian cancer cells (MDAH2774) transfected with various concentrations of STIP1 polypeptide 520-543 (Peptide 520) and other STIP1 polypeptides.

|  | Negative Control | Peptide 520 25 uM | Peptide 520 150 uM | Peptide 520 200 uM | Peptide 445 200 uM | Peptide 458 200 uM | Peptide 495 200 uM |
|---|---|---|---|---|---|---|---|
| Original O.D | 0.15 | 0.15 | 0.10 | 0.09 | 0.13 | 0.13 | 0.14 |
| Normalized O.D | 1 | 1.02 | 0.49 | 0.29 | 0.86 | 0.83 | 0.97 |
| Cell viability (%) | 100 | 102.14 | 49.03 | 28.64 | 85.73 | 82.57 | 96.94 |

Figure 10B:
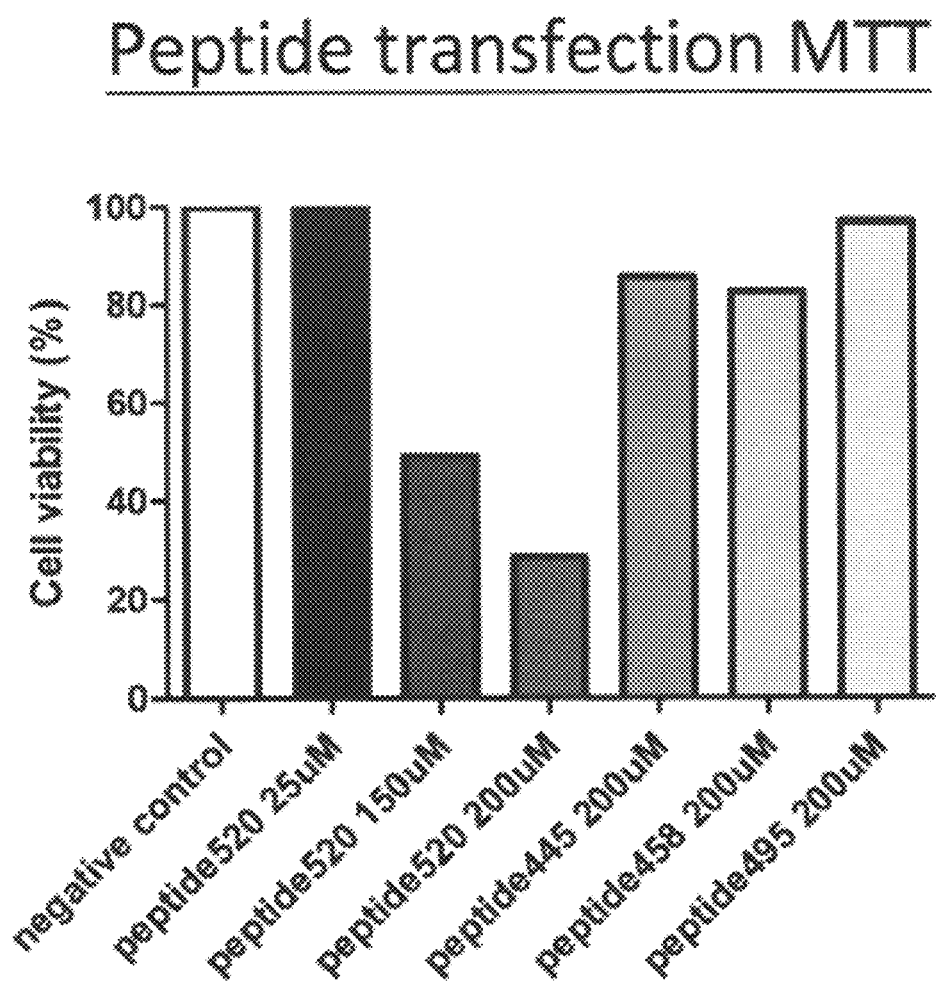
FIG. 10B illustrates cancer cell (MDAH2774) viability in groups treated with various concentrations of STIP1 polypeptide 520-543 (SEQ ID NO:1) and other STIP1 polypeptides (SEQ ID NO: 26, 27 and 29).

FIG. 10B and Table 2 show that STIP1 polypeptide 520-543 suppresses cancer cell viability in a dose-dependent fashion, whereas STIP1 polypeptides comprising other amino acid sequences 445-469 (peptide 445; SEQ ID NO: 26), 458-482 (peptide 458; SEQ ID NO: 27) and 495-519 (peptide 495; SEQ ID NO:29) did not significantly suppress cancer cell viability. Without being bound by any theory, it is believed that STIP1 polypeptide 520-543 (SEQ ID NO:1) competitively inhibits STIP1 antibody.

Conclusion: Results in FIGS. 9A to FIG. 10B indicate that suppressing STIP1 led to reduced cell viability. STIP1 can be suppressed by using an STIP1 antibody that binds to the an epitope comprising SEQ ID NO:1, or by administering an isolated STIP1 polypeptide having SEQ ID NO:1.

Cell Permeability of STIP1 Polypeptide 520-543 (SEQ ID NO:1)

To verify the cancer cell permeability of STIP1 polypeptide 520-543, ovarian cancer cells (MDAH2774) were treated with 10 uM of STIP1 polypeptide 520-543 having eight D-arginine residues for 24 hrs. The intracellular distribution of STIP1 polypeptide 520-543 was examined using anti-myc antibody under immunofluorescent microscopy. FIG. 11B shows the presence of STIP1 polypeptide 520-543 in the cytosol of the ovarian cancer cell.

The Effect of STIP1 Polypeptide 520-543 on HSP90/STIP1 Interaction

The effect of STIP1 polypeptide 520-543 on HSP90 and STIP1 interaction was evaluated by treating cancer cells with various concentrations of STIP1 polypeptide 520-543. HSP90-STIP1 interaction with evaluated using immunoprecipitation method.

Figure 12:
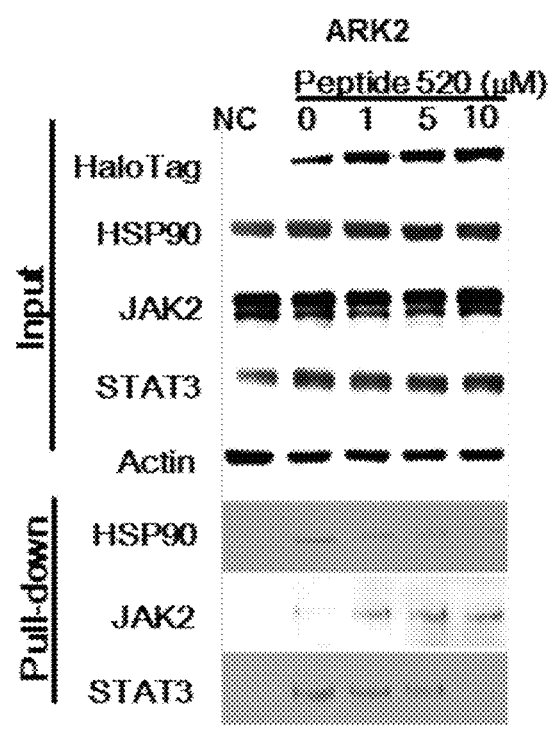
FIG. 12 shows the effect of STIP1 polypeptide 520-543 on HSP90 and STIP1 interaction.

FIG. 12 shows the binding ability of STIP1 to HSP90 was reduced as the concentration of STIP1 polypeptide 520-543 increased. This data shows STIP1 polypeptide 520-543 can prevent STIP1 binding to HSP90 and client protein misfolding.

The Effect of STIP1 Polypeptide 520-543 on Cancer Cells

An in vitro evaluation of the effect of STIP1 polypeptide 520-543 on cancer cells was performed.

Cell permeable STIP1 polypeptide 520-543 was added to the following cancer cell lines: MDAH2774 (ovarian cancer); ARK2 (endometrial cancer); NPC-BM1 (nasopharyngeal cancer); SAS (oral cancer); Colon 205 (colon cancer); CL 1-0 (lung cancer); BxPC3 (pancreatic cancer); HepG2 (liver cancer) and MCF7 (breast cancer) cells. Cancer cell viability was assessed using the MTT assay and cell death was assessed using LDH assay.

Figure 13:
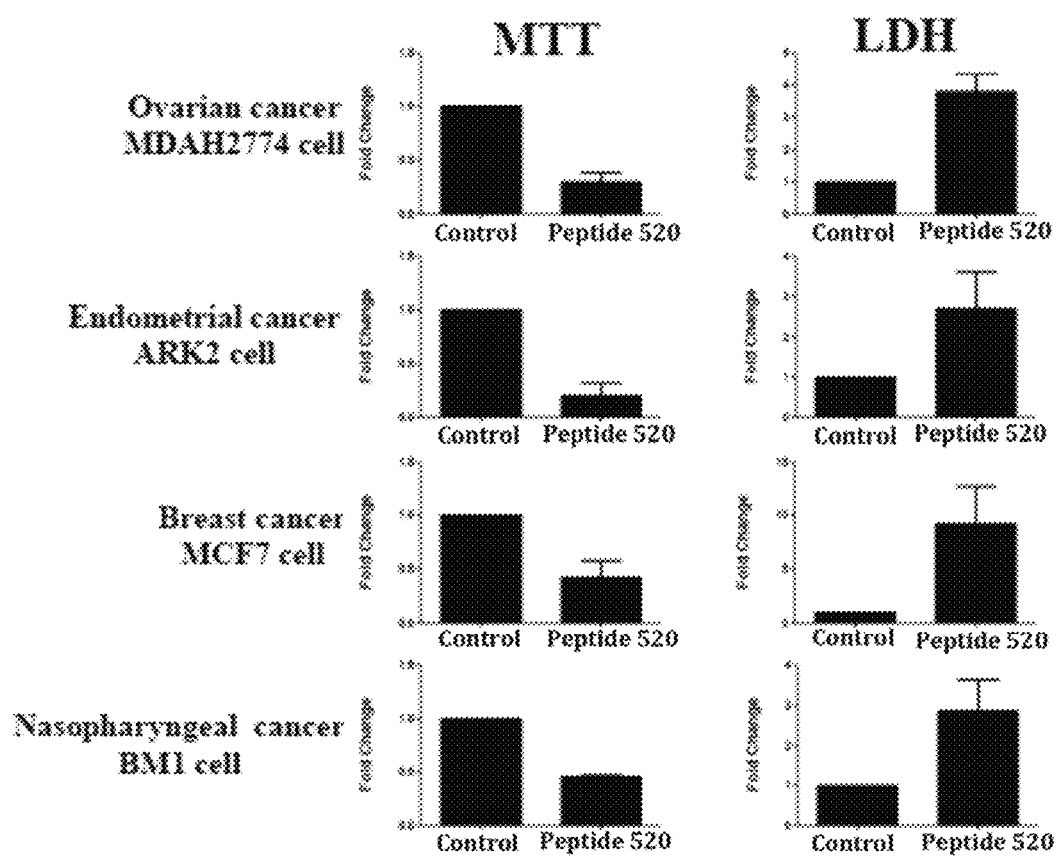
FIG. 13A and FIG. 13B are bar graphs illustrating the effect of STIP1 polypeptide 520-543 (peptide 520) on LDH activity and MTT activity of the tested cancer cell lines.
Figure 13:
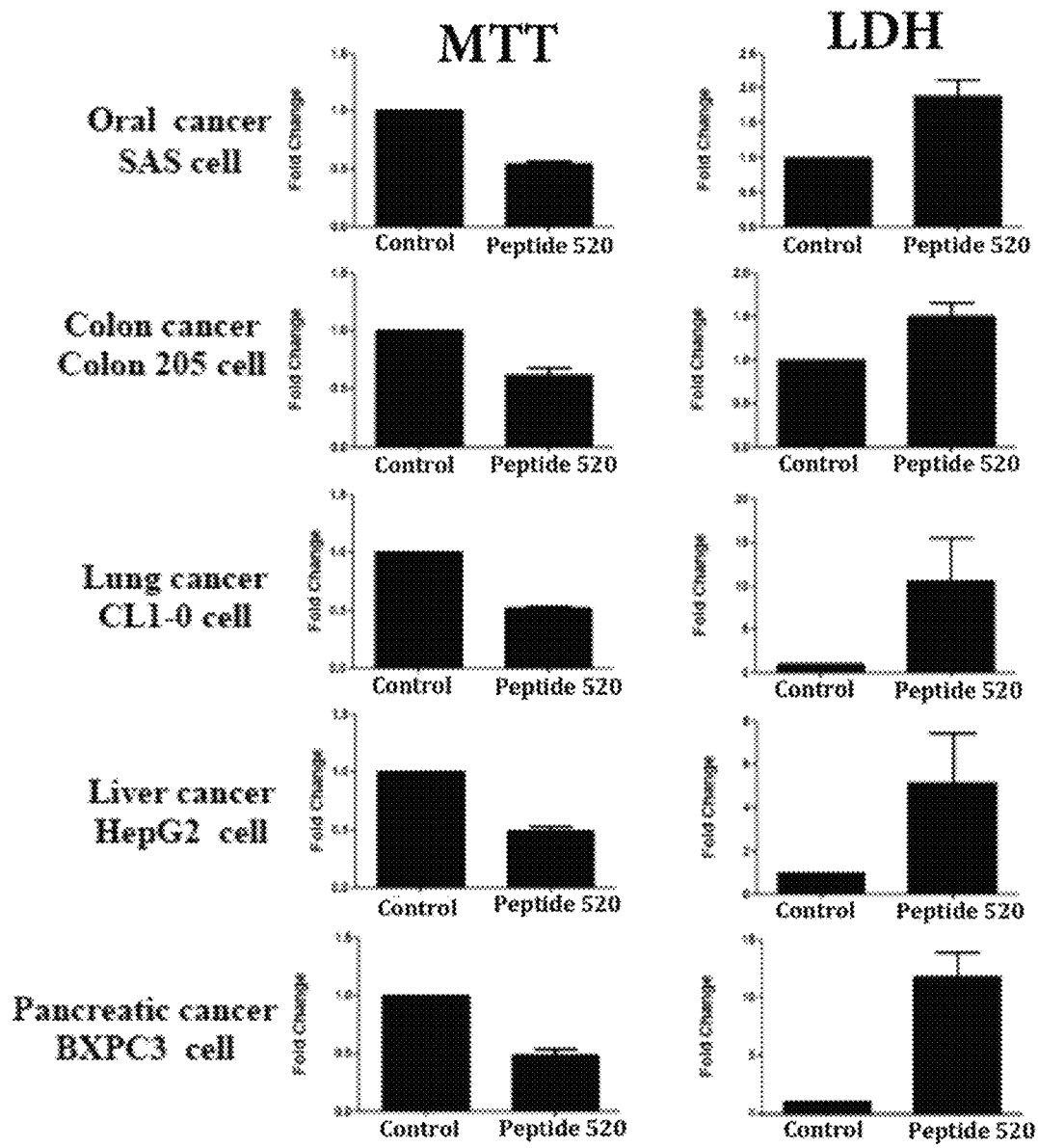

FIG. 13A and FIG. 13B show cell permeable STIP1 polypeptide 520-543 (peptide 520) inhibits cell proliferation (illustrated by reduced MTT activity) and induce cell death (illustrated by increased LDH activity) in all of the tested cancer cells.

An in vivo evaluation of the effect of STIP1 polypeptide 520-543 on nude mice was performed.

Nude mice were inoculated with $5 \times 10^5$ cells of human ovarian cancer cells MDAH2774 subcutaneously. 100 μg of STIP1 polypeptide 520-543 was administered three times a week via the tail vein.

Figure 14:
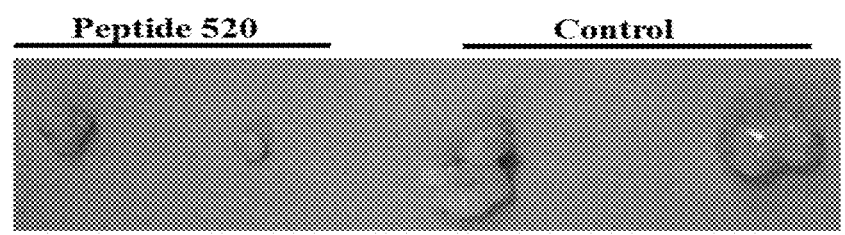
FIG. 14 shows the size of the tumor mass in mice treated with STIP1 polypeptide 520-543 (peptide 520) as compared with a control.

FIG. 14 illustrates the size of the tumor mass in mice treated with STIP1 polypeptide 520-543 is less than that of the control group. These results indicate the in vivo efficacy of STIP1 polypeptide 520-543 in reducing cancer cells.

STIP1 Polypeptide 520-543 Induces the Degradation of JAK2 Protein

One of HSP90 client proteins is JAK2 (Frid et al. JAK-STAT 1(2):77 (2012); Marubayashi et al. J. Clin. Invest. 120(10):3578 (2010). The JAK2-STAT3 pathway plays an important role in tumor transformation and progression (Miklossy et al., Nat Rev. Drug Discovery: 12(8):611 (2013)).

The effect of STIP1 polypeptide 520-543 on HSP90 function was evaluated using ovarian cancer cell line (MDAH2774) and endometrial cancer cell line (ARK2). The cancer cell lines were treated various concentrations of STIP1 polypeptide 520-543.

Forty-eight hours later, the intracellular levels of JAK2 and phosphor-STAT3 were decreased in dose dependent manner, as illustrated in FIG. 15A. In addition, JAK2 and Bc1-XL proteins were down-regulated in presence of STIP1 polypeptide 520-543, as illustrated by western blot in FIG. 15B. These results demonstrate that STIP1 polypeptide 520-543 induces cell death by blocking the JAK2-STAT3-Bc1 XL pathway.

Production of Monoclonal Antibodies Reactive to SEQ ID NO:1 Polypeptide

BALB/c mice will be immunized intraperitoneally 3-4 times at 2-4 weekly intervals, with SEQ ID NO:1 polypeptide and challenged 3 days prior to spleen-cell removal with SEQ ID NO:1 polypeptide. A spleen-cell suspension will be prepared, fused with the myeloma NS1/1 AG4.1 and hybridomas grown up and cloned. Initially, hybridoma culture supernatants will be tested for reactivity with SEQ ID NO:1 polypeptide by immunofluorescence flow cytometry (FACS). Briefly, SEQ ID NO:1 polypeptide will be incubated (30 min, 4.degree. C.) with undiluted hybridoma supernatant, washed and incubated with fluorescein-isothiocyanate (FITC)-sheep F(ab')2 anti-mouse Ig(100 ug/ml). Following final washing, monoclonal antibody binding to SEQ ID NO:1 polypeptide will be examined by FACS analysis. Positive hybridoma supernatants will be screened on the human melanoma cell line MM-170 to eliminate non-endothelial specific mAbs. Binding specificity to SEQ ID NO:1 polypeptide will be further confirmed by screening of monoclonal antibodies on a panel of human tumor cell lines as well as human lymphocytes, monocytes, neutrophils, red cells and platelets.

All references cited and discussed in this specification are incorporated herein by reference in their entirety. Variations, modifications and other implementations of what is described herein will occur to those of ordinary skill m the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

Sequence Listing
Stress-induced phosphoprotein 1 peptide 520
(amino acid position 520-543 of full-length
STIP1)
SEQ ID NO: 1
EHLKNPVIAQKIQKLMDVGLIAIR Stress-induced phosphoprotein 1 peptide 482
(amino acid position 482-506 of full-length
STIP1)
SEQ ID NO: 2
PEDVKRRAMADPEVQQIMSDPAMRL Stress-induced phosphoprotein 1 [Homo sapiens]|
GenBank Accession No. NP_006810
SEQ ID NO: 3
MEQVNELKEKGNKALSVGNIDDALQCYSEAIKLDPHNHVLYSNRSAAYAK

KGDYQKAYEDGCKTVDLKPDWGKGYSRKAAALEFLNRFEEAKRTYEEGLK

HEANNPQLKEGLQNMEARLAERKFMNPFNMPNLYQKLESDPRTRTLLSDP

TYRELIEQLRNKPSDLGTKLQDPRIMTTLSVLLGVDLGSMDEEEEIATPP

PPPPPKKETKPEPMEEDLPENKKQALKEKELGNDAYKKKDFDTALKHYDK

AKELDPTNMTYITNQAAVYFEKGDYNKCRELCEKAIEVGRENREDYRQIA

KAYARIGNSYFKEEKYKDAIHFYNKSLAEHRTPDVLKKCQQAEKILKEQE

RLAYINPDLALEEKNKGNECFQKGDYPQAMKHYTEAIKRNPKDAKLYSNR

AACYTKLLEFQLALKDCEECIQLEPTFIKGYTRKAAALEAMKDYTKAMDV

YQKALDLDSSCKEAADGYQRCMMAQYNRHDSPEDVKRRAMADPEVQQIMS

DPAMRLILEQMQKDPQALSEHLKNPVIAQKIQKLMDVGLIAIR

STIP1 peptide from cancer cell line
SEQ ID NO: 4
DPQALSEHLK

STIP1 peptide from cancer cell line
SEQ ID NO: 5
AMADPEVQQIMSDPAMR

STIP1 peptide from cancer cell line
SEQ ID NO: 6
AALEFLNR

STIP1 peptide from cancer cell line
SEQ ID NO: 7
TYEEGLKHEANNPQLK

STIP1 peptide from cancer cell line
SEQ ID NO: 8
LILEQMQK

STIP1 peptide from cancer cell line
SEQ ID NO: 9
LDPHNHVLYSNR

STIP1 peptide from cancer cell line
SEQ ID NO: 10
LAYINPDLALEEK

STIP1 peptide from cancer cell line
SEQ ID NO: 11
LMDVGLIAIR

STIP1 peptide from cancer cell line
SEQ ID NO: 12
NPVIAQKIQKLMDVGLIAIR

STIP1 peptide from cancer cell line
SEQ ID NO: 13
EGLQNMEAR

STIP1 peptide from cancer cell line
SEQ ID NO: 14
DCEECIQLEPTFIK

STIP1 peptide from cancer cell line
SEQ ID NO: 15
LLEFQLALK

STIP1 peptide from cancer cell line
SEQ ID NO: 16
KAAALEFLNR

STIP1 peptide from cancer cell line
SEQ ID NO: 17
ALDLDSSCK

-continued

STIP1 peptide from cancer cell line  SEQ ID NO: 18
FMNPFNMPNLYQK

STIP1 peptide from cancer cell line  SEQ ID NO: 19
ALSVGNIDDALQCYSEAIK

STIP1 peptide from cancer cell line  SEQ ID NO: 20
HYTEAIK

STIP1 peptide from cancer cell line  SEQ ID NO: 21
NPVIAQK

STIP1 peptide from cancer cell line  SEQ ID NO: 22
TLLSDPTYR

STIP1 peptide from cancer cell line  SEQ ID NO: 23
HDSPEDVKR

STIP1 peptide from cancer cell line  SEQ ID NO: 24
DAIHFYNK

STIP1 peptide from cancer cell line  SEQ ID NO: 25
KDFDTALK

STIP1 peptide 445 (amino acid position 445-469 of full-length STIP1)  SEQ ID NO: 26
TKAMDVYQKALDLDSSCKEAADGYQ STIP1 peptide 458 (amino acid position 458-482 of full-length STIP1)  SEQ ID NO: 27
DSSCKEAADGYQRCMMAQYNRHDSP STIP1 peptide 470 (amino acid position 470-494 of full-length STIP1)  SEQ ID NO: 28
RCMMAQYNRHDSPEDVKRRAMADPE STIP1 peptide 495 (amino acid position 495-519 of full-length STIP1)  SEQ ID NO: 29
VQQIMSDPAMRLILEQMQKDPQALS STIP1 peptide 507 (amino acid position 507-531 of full-length STIP1)  SEQ ID NO: 30
ILEQMQKDPQALSEHLKNPVIAQKI

---

What is claimed is:

1. A method for inhibiting cancer cell growth, comprising the step of administering an effective amount of isolated polypeptide comprising the amino acid sequence SEQ ID NO: 1 to a subject in need thereof, wherein the cancer cell expresses STIP1.

2. The method of claim 1 wherein the cancer is selected from the group consisting of pancreatic cancer, endometrial cancer, lung cancer, nasopharyngeal carcinoma, breast cancer and colon cancer.

3. The method of claim 1 further comprising the step of administering an antibody against STIP1.

4. A method for inhibiting cancer cell growth in a subject, the method comprising the step of administering an effective amount of an antibody, or an antigen-binding portion thereof, binding to the peptide having the amino acid sequence of SEQ ID NO: 1, wherein the cancer cell expresses STIP1.

5. The method of claim 4 wherein the cancer is selected from the group consisting of pancreatic cancer, endometrial cancer, lung cancer, nasopharyngeal carcinoma, breast cancer and colon cancer.

6. The method of claim 4 further comprising administering an isolated polypeptide comprising an amino acid sequence of SEQ ID NO: 1.

* * * * *

SEQUENCE LISTING

<160> NUMBER OF SEQ ID NOS: 30

<210> SEQ ID NO 1
<211> LENGTH: 24
<212> TYPE: PRT
<213> ORGANISM: homo sapiens

<400> SEQUENCE: 1

Glu His Leu Lys Asn Pro Val Ile Ala Gln Lys Ile Gln Lys Leu Met
1               5                   10                  15

Asp Val Gly Leu Ile Ala Ile Arg
            20

<210> SEQ ID NO 2
<211> LENGTH: 25
<212> TYPE: PRT
<213> ORGANISM: homo sapiens

<400> SEQUENCE: 2

Pro Glu Asp Val Lys Arg Arg Ala Met Ala Asp Pro Glu Val Gln Gln
1               5                   10                  15

Ile Met Ser Asp Pro Ala Met Arg Leu
            20                  25

<210> SEQ ID NO 3
<211> LENGTH: 543
<212> TYPE: PRT
<213> ORGANISM: homo sapiens

<400> SEQUENCE: 3

Met Glu Gln Val Asn Glu Leu Lys Glu Lys Gly Asn Lys Ala Leu Ser
1               5                   10                  15

Val Gly Asn Ile Asp Asp Ala Leu Gln Cys Tyr Ser Glu Ala Ile Lys
            20                  25                  30

Leu Asp Pro His Asn His Val Leu Tyr Ser Asn Arg Ser Ala Ala Tyr
        35                  40                  45

-continued

Ala Lys Lys Gly Asp Tyr Gln Lys Ala Tyr Glu Asp Gly Cys Lys Thr
 50                  55                  60

Val Asp Leu Lys Pro Asp Trp Gly Lys Gly Tyr Ser Arg Lys Ala Ala
 65                  70                  75                  80

Ala Leu Glu Phe Leu Asn Arg Phe Glu Ala Lys Arg Thr Tyr Glu
                 85                  90                  95

Glu Gly Leu Lys His Glu Ala Asn Asn Pro Gln Leu Lys Glu Gly Leu
                100                 105                 110

Gln Asn Met Glu Ala Arg Leu Ala Glu Arg Lys Phe Met Asn Pro Phe
            115                 120                 125

Asn Met Pro Asn Leu Tyr Gln Lys Leu Glu Ser Asp Pro Arg Thr Arg
        130                 135                 140

Thr Leu Leu Ser Asp Pro Thr Tyr Arg Glu Leu Ile Glu Gln Leu Arg
145                 150                 155                 160

Asn Lys Pro Ser Asp Leu Gly Thr Lys Leu Gln Asp Pro Arg Ile Met
                165                 170                 175

Thr Thr Leu Ser Val Leu Leu Gly Val Asp Leu Gly Ser Met Asp Glu
            180                 185                 190

Glu Glu Glu Ile Ala Thr Pro Pro Pro Pro Pro Pro Lys Lys Glu
        195                 200                 205

Thr Lys Pro Glu Pro Met Glu Glu Asp Leu Pro Glu Asn Lys Lys Gln
210                 215                 220

Ala Leu Lys Glu Lys Glu Leu Gly Asn Asp Ala Tyr Lys Lys Lys Asp
225                 230                 235                 240

Phe Asp Thr Ala Leu Lys His Tyr Asp Lys Ala Lys Glu Leu Asp Pro
                245                 250                 255

Thr Asn Met Thr Tyr Ile Thr Asn Gln Ala Ala Val Tyr Phe Glu Lys
            260                 265                 270

Gly Asp Tyr Asn Lys Cys Arg Glu Leu Cys Glu Lys Ala Ile Glu Val
        275                 280                 285

Gly Arg Glu Asn Arg Glu Asp Tyr Arg Gln Ile Ala Lys Ala Tyr Ala
290                 295                 300

Arg Ile Gly Asn Ser Tyr Phe Lys Glu Lys Tyr Lys Asp Ala Ile
305                 310                 315                 320

His Phe Tyr Asn Lys Ser Leu Ala Glu His Arg Thr Pro Asp Val Leu
                325                 330                 335

Lys Lys Cys Gln Gln Ala Glu Lys Ile Leu Lys Glu Gln Glu Arg Leu
            340                 345                 350

Ala Tyr Ile Asn Pro Asp Leu Ala Leu Glu Glu Lys Asn Lys Gly Asn
        355                 360                 365

Glu Cys Phe Gln Lys Gly Asp Tyr Pro Gln Ala Met Lys His Tyr Thr
370                 375                 380

Glu Ala Ile Lys Arg Asn Pro Lys Asp Ala Lys Leu Tyr Ser Asn Arg
385                 390                 395                 400

Ala Ala Cys Tyr Thr Lys Leu Leu Glu Phe Gln Leu Ala Leu Lys Asp
                405                 410                 415

Cys Glu Glu Cys Ile Gln Leu Glu Pro Thr Phe Ile Lys Gly Tyr Thr
            420                 425                 430

Arg Lys Ala Ala Ala Leu Glu Ala Met Lys Asp Tyr Thr Lys Ala Met
        435                 440                 445

Asp Val Tyr Gln Lys Ala Leu Asp Leu Asp Ser Ser Cys Lys Glu Ala
450                 455                 460

Ala Asp Gly Tyr Gln Arg Cys Met Met Ala Gln Tyr Asn Arg His Asp

-continued

```
            465                 470                 475                 480
Ser Pro Glu Asp Val Lys Arg Arg Ala Met Ala Asp Pro Glu Val Gln
                485                 490                 495
Gln Ile Met Ser Asp Pro Ala Met Arg Leu Ile Leu Glu Gln Met Gln
            500                 505                 510
Lys Asp Pro Gln Ala Leu Ser Glu His Leu Lys Asn Pro Val Ile Ala
        515                 520                 525
Gln Lys Ile Gln Lys Leu Met Asp Val Gly Leu Ile Ala Ile Arg
    530                 535                 540

<210> SEQ ID NO 4
<211> LENGTH: 10
<212> TYPE: PRT
<213> ORGANISM: homo sapiens

<400> SEQUENCE: 4

Asp Pro Gln Ala Leu Ser Glu His Leu Lys
1               5                   10

<210> SEQ ID NO 5
<211> LENGTH: 17
<212> TYPE: PRT
<213> ORGANISM: homo sapiens

<400> SEQUENCE: 5

Ala Met Ala Asp Pro Glu Val Gln Gln Ile Met Ser Asp Pro Ala Met
1               5                   10                  15

Arg

<210> SEQ ID NO 6
<211> LENGTH: 8
<212> TYPE: PRT
<213> ORGANISM: homo sapiens

<400> SEQUENCE: 6

Ala Ala Leu Glu Phe Leu Asn Arg
1               5

<210> SEQ ID NO 7
<211> LENGTH: 16
<212> TYPE: PRT
<213> ORGANISM: homo sapiens

<400> SEQUENCE: 7

Thr Tyr Glu Glu Gly Leu Lys His Glu Ala Asn Asn Pro Gln Leu Lys
1               5                   10                  15

<210> SEQ ID NO 8
<211> LENGTH: 8
<212> TYPE: PRT
<213> ORGANISM: homo sapiens

<400> SEQUENCE: 8

Leu Ile Leu Glu Gln Met Gln Lys
1               5

<210> SEQ ID NO 9
<211> LENGTH: 12
<212> TYPE: PRT
<213> ORGANISM: homo sapiens

<400> SEQUENCE: 9
```

-continued

Leu Asp Pro His Asn His Val Leu Tyr Ser Asn Arg
1               5                   10

<210> SEQ ID NO 10
<211> LENGTH: 13
<212> TYPE: PRT
<213> ORGANISM: homo sapiens

<400> SEQUENCE: 10

Leu Ala Tyr Ile Asn Pro Asp Leu Ala Leu Glu Glu Lys
1               5                   10

<210> SEQ ID NO 11
<211> LENGTH: 10
<212> TYPE: PRT
<213> ORGANISM: homo sapiens

<400> SEQUENCE: 11

Leu Met Asp Val Gly Leu Ile Ala Ile Arg
1               5                   10

<210> SEQ ID NO 12
<211> LENGTH: 20
<212> TYPE: PRT
<213> ORGANISM: homo sapiens

<400> SEQUENCE: 12

Asn Pro Val Ile Ala Gln Lys Ile Gln Lys Leu Met Asp Val Gly Leu
1               5                   10                  15

Ile Ala Ile Arg
            20

<210> SEQ ID NO 13
<211> LENGTH: 9
<212> TYPE: PRT
<213> ORGANISM: homo sapiens

<400> SEQUENCE: 13

Glu Gly Leu Gln Asn Met Glu Ala Arg
1               5

<210> SEQ ID NO 14
<211> LENGTH: 14
<212> TYPE: PRT
<213> ORGANISM: homo sapiens

<400> SEQUENCE: 14

Asp Cys Glu Glu Cys Ile Gln Leu Glu Pro Thr Phe Ile Lys
1               5                   10

<210> SEQ ID NO 15
<211> LENGTH: 9
<212> TYPE: PRT
<213> ORGANISM: homo sapiens

<400> SEQUENCE: 15

Leu Leu Glu Phe Gln Leu Ala Leu Lys
1               5

<210> SEQ ID NO 16
<211> LENGTH: 10
<212> TYPE: PRT
<213> ORGANISM: homo sapiens

<400> SEQUENCE: 16

```
Lys Ala Ala Ala Leu Glu Phe Leu Asn Arg
1               5                   10

<210> SEQ ID NO 17
<211> LENGTH: 9
<212> TYPE: PRT
<213> ORGANISM: homo sapiens

<400> SEQUENCE: 17

Ala Leu Asp Leu Asp Ser Ser Cys Lys
1               5

<210> SEQ ID NO 18
<211> LENGTH: 13
<212> TYPE: PRT
<213> ORGANISM: homo sapiens

<400> SEQUENCE: 18

Phe Met Asn Pro Phe Asn Met Pro Asn Leu Tyr Gln Lys
1               5                   10

<210> SEQ ID NO 19
<211> LENGTH: 19
<212> TYPE: PRT
<213> ORGANISM: homo sapiens

<400> SEQUENCE: 19

Ala Leu Ser Val Gly Asn Ile Asp Asp Ala Leu Gln Cys Tyr Ser Glu
1               5                   10                  15

Ala Ile Lys

<210> SEQ ID NO 20
<211> LENGTH: 7
<212> TYPE: PRT
<213> ORGANISM: homo sapiens

<400> SEQUENCE: 20

His Tyr Thr Glu Ala Ile Lys
1               5

<210> SEQ ID NO 21
<211> LENGTH: 7
<212> TYPE: PRT
<213> ORGANISM: homo sapiens

<400> SEQUENCE: 21

Asn Pro Val Ile Ala Gln Lys
1               5

<210> SEQ ID NO 22
<211> LENGTH: 9
<212> TYPE: PRT
<213> ORGANISM: homo sapiens

<400> SEQUENCE: 22

Thr Leu Leu Ser Asp Pro Thr Tyr Arg
1               5

<210> SEQ ID NO 23
<211> LENGTH: 9
<212> TYPE: PRT
<213> ORGANISM: homo sapiens

<400> SEQUENCE: 23
```

```
His Asp Ser Pro Glu Asp Val Lys Arg
1               5
```

<210> SEQ ID NO 24
<211> LENGTH: 8
<212> TYPE: PRT
<213> ORGANISM: homo sapiens

<400> SEQUENCE: 24

```
Asp Ala Ile His Phe Tyr Asn Lys
1               5
```

<210> SEQ ID NO 25
<211> LENGTH: 8
<212> TYPE: PRT
<213> ORGANISM: homo sapiens

<400> SEQUENCE: 25

```
Lys Asp Phe Asp Thr Ala Leu Lys
1               5
```

<210> SEQ ID NO 26
<211> LENGTH: 25
<212> TYPE: PRT
<213> ORGANISM: homo sapiens

<400> SEQUENCE: 26

```
Thr Lys Ala Met Asp Val Tyr Gln Lys Ala Leu Asp Leu Asp Ser Ser
1               5                   10                  15

Cys Lys Glu Ala Ala Asp Gly Tyr Gln
            20                  25
```

<210> SEQ ID NO 27
<211> LENGTH: 25
<212> TYPE: PRT
<213> ORGANISM: homo sapiens

<400> SEQUENCE: 27

```
Asp Ser Ser Cys Lys Glu Ala Ala Asp Gly Tyr Gln Arg Cys Met Met
1               5                   10                  15

Ala Gln Tyr Asn Arg His Asp Ser Pro
            20                  25
```

<210> SEQ ID NO 28
<211> LENGTH: 25
<212> TYPE: PRT
<213> ORGANISM: homo sapiens

<400> SEQUENCE: 28

```
Arg Cys Met Met Ala Gln Tyr Asn Arg His Asp Ser Pro Glu Asp Val
1               5                   10                  15

Lys Arg Arg Ala Met Ala Asp Pro Glu
            20                  25
```

<210> SEQ ID NO 29
<211> LENGTH: 25
<212> TYPE: PRT
<213> ORGANISM: homo sapiens

<400> SEQUENCE: 29

```
Val Gln Gln Ile Met Ser Asp Pro Ala Met Arg Leu Ile Leu Glu Gln
1               5                   10                  15
```

```
Met Gln Lys Asp Pro Gln Ala Leu Ser
            20                  25

<210> SEQ ID NO 30
<211> LENGTH: 25
<212> TYPE: PRT
<213> ORGANISM: homo sapiens

<400> SEQUENCE: 30

Ile Leu Glu Gln Met Gln Lys Asp Pro Gln Ala Leu Ser Glu His Leu
1               5                   10                  15

Lys Asn Pro Val Ile Ala Gln Lys Ile
            20                  25
```